United States Patent
Schussler

(10) Patent No.: US 12,173,321 B2
(45) Date of Patent: Dec. 24, 2024

(54) MATERIAL AND METHOD FOR STORING, TRANSFERRING AND DELIVERING MESENCHYMAL STEM CELLS WHICH ARE IMMEDIATELY AVAILABLE AND FUNCTIONAL IN THE CONTEXT OF A MYOCARDIAL INFARCTION

(71) Applicant: Olivier Schussler, Messery (FR)

(72) Inventor: Olivier Schussler, Messery (FR)

( * ) Notice: Subject to any disclaimer, the term of this patent is extended or adjusted under 35 U.S.C. 154(b) by 7 days.

(21) Appl. No.: 16/639,582

(22) PCT Filed: Jun. 11, 2018

(86) PCT No.: PCT/FR2018/000168
§ 371 (c)(1),
(2) Date: Feb. 16, 2020

(87) PCT Pub. No.: WO2019/038484
PCT Pub. Date: Feb. 28, 2019

(65) Prior Publication Data
US 2022/0081677 A1    Mar. 17, 2022

(30) Foreign Application Priority Data
Aug. 25, 2017 (FR) ........................ 1757884

(51) Int. Cl.
| | | |
|---|---|---|
| C12N 5/077 | (2010.01) | |
| A61L 27/38 | (2006.01) | |
| A61L 27/54 | (2006.01) | |
| A61L 27/56 | (2006.01) | |

(52) U.S. Cl.
CPC ........ *C12N 5/0657* (2013.01); *A61L 27/3826* (2013.01); *A61L 27/3834* (2013.01); *A61L 27/54* (2013.01); *A61L 27/56* (2013.01); *A61L 2430/20* (2013.01); *C12N 2501/10* (2013.01); *C12N 2501/11* (2013.01); *C12N 2501/15* (2013.01); *C12N 2501/2301* (2013.01); *C12N 2501/24* (2013.01); *C12N 2501/25* (2013.01); *C12N 2506/1346* (2013.01); *C12N 2513/00* (2013.01); *C12N 2533/54* (2013.01)

(58) Field of Classification Search
CPC .............. C12N 5/0657; C12N 2501/10; C12N 2501/11; C12N 2501/15; C12N 2501/2301; C12N 2501/24; C12N 2501/25; C12N 2506/1346; C12N 2513/00; C12N 2533/54; A61L 27/3826; A61L 27/3834; A61L 27/54; A61L 27/56; A61L 2430/20
See application file for complete search history.

(56) References Cited

PUBLICATIONS

Sivanathan et al., Interferon-gamma modification of mesenchymal stem cells: implications of autologous and allogenic mesenchymal stem cells therapy allotransplantation, Stem Cell Reviews and Reports, 10: 351-375. (Year: 2014).*
Rouhi, et al., Autologous serum enhances cardiomyocyte differentiation of rat bone marrow mesenchymal stem cells in the presence of transforming growth factor-beta1 (TGF-beta1), 49: 287-294. (Year: 2013).*
Israeli-Rosenberg, Integrins and integrin-associated proteins in the cardiac myocyte, Circulation Research, p. 572-586. (Year: 2014).*
Kern, et al., Up-regulation of alpha-smooth muscle actin in cardiomyocytes from non-hypertrophic and non-failing transgenic mouse hearts expressing N-terminal truncated cardiac troponin I, FEBS Open Bio, 4: p. 11-17. (Year: 2014).*
Engler et al., matrix elasticity directs stem cell lineage specification, Cell, 126: 677-689. (Year: 2006).*
Valiunas et al, Human mesenchymal stem cells make cardiac connexins and form functional gap junctions, Journal of Physiology, 555(3): 617-626. (Year: 2004).*
Bellis et al., Advantages of RGD peptides for directing cell association with biomaterials, Biomaterials, 32: 4205-4210. (Year: 2011).*
Suchy et al., The effect of different ceoss-linking conditions on collagen-based nanocomposite scaffolds—an in vitro evaluation using mesenchymal stem cells, Biomedical Materials, 10: p. 1-14. (Year: 2015).*
Schussler et al., Use of arginine-glycine-aspartic acid adhesion peptides coupled with a new collagen scaffold to engineer a myocardium-like tissue graft, Nature Clinical Practice Cardiovascular Medicine, 6(3): 240-248. (Year: 2009).*
Wu et al., Ascorbic acid promotes extracellular matrix deposition while preserving valve interstitial cell quiescence within 3D hydrogel scaffolds, Journal of Tissue Engineering and Regenerative Medicine, 11: 1963-1973. (Year: 2015).*
Radisic et al., Pre-treatment of synthetic elastomeric scaffolds by cardiac fibroblasts improves engineered heart tissue. Journal of Biomedical Materials and Research Part A, p. 713-724. (Year: 2007).*
Desai et al., Reversible Modulation of Myofibroblast Differentiation in Adipose-Derived Mesenchymal Stem Cells, PLOS One, 9(1): 1-12 (Year: 2014).*
Cherng et al., Alpha-Smooth Muscle Actin (α-SMA), The Journal of American Science, 4(4): 7-9 (Year: 2008).*
Dominici et al., Position Paper Minimal criteria for defining multipotent mesenchymal stromal cells. The International Society for Cellular Therapy position statement, Cytotherapy, 2006, 8(4): 315-317. (Year: 2006).*
Boland et al., The role of basement membranes in cardiac biology and disease, Bioscience Reports, 41: 1-21 (Year: 2021).*
Jain et al., Mimicking the Natural Basement Membrane for Advanced Tissue Engineering, BioMacromolecules, 23: 3081-3104. (Year: 2022).*

(Continued)

*Primary Examiner* — Arthur S Leonard
*Assistant Examiner* — Joseph Paul Miano
(74) *Attorney, Agent, or Firm* — Rivka Friedman

(57) ABSTRACT

The application describes a contractile cellular biomaterial that is particularly well suited to regenerative therapy of tissue affected by myocardial infraction. The biomaterial comprises a contractile tissue which is contained in an optionally porous solid substrate. The contractile tissue is formed by differentiating stem cells, in particular mesenchymal stem cells. In addition to being contractile, the biomaterial can have inducible paracrine activity. The biomaterial has, in particular, the advantage of not needing to be frozen in order to be conserved.

15 Claims, 4 Drawing Sheets
Specification includes a Sequence Listing.

(56) References Cited

PUBLICATIONS

Rippel et al., Tissue-Engineered Heart Valve: Future of Cardiac Surgery, World J Surg, 36: 1581-1592. (Year: 2012).*

Zhou et al., Inhibition of SRF/myocardin reduces aortic stiffness by targeting vascular smooth muscle cell stiffening in hypertension, Cardiovascular Research, 113: 171-182. (Year: 2017).*

Woodcock et al., Cells in focus: Cardiomyocytes structure, function and associated pathologies, The International Journal of Biochemistry & Cell Biology, 37: 1746-1751. (Year: 2005).*

Seow et al., Hill's equation of muscle performance and its hidden insight on molecular mechanisms, The Journal of General Physiology, 142(6): 361-573. (Year: 2013).*

Khalpey et al., Robotic Assisted Implantation of Ventricular Assist Device after Sternectomy & Pectoralis Muscle Flap, Asaio J, p. 1-6. (Year: 2014).*

Dias-Flores et al., Review Pericytes. Morphofunction, interactions and pathology in a quiescent and activated mesenchymal cell niche, Histol Histopathol, 24: 909-969. (Year: 2009).*

Melham et al., Endothelial Cell Indoleamine 2, 3-Dioxygenase 1 Alters Cardiac Function After Myocardial Infarction Through Kynurenine, Circulation, 143: 566-580. (Year: 2021).*

Adham et al., Mechanical Characteristics of Fresh and Frozen Human Descending Thoracic Aorta, Journal of Surgical Research, 64: 32-34. (Year: 1996).*

Callahan et al., Maximizing phenotype constraint and extracellular matrix production in primary human chondrocytes using arginine-glycine-aspartate concentration gradient hydrogels, Acta Biomaterialia, p. 7420-7428. (Year: 2013).*

Lin, Yu-Li et al., "Stiffness-Controlled Three-Dimensional Collagen Scaffolds for Differetiation of Human Wharton's Jelly Mesenchymal Stem Cells Into Cardiac Progenitor Cells: Collagen Scaffold for MSC Differentiate Into Cardiomyogenic Cells," Journal of Biomedical Materials Research Part A., (May 6, 2016), pp. 2234-2242, vol. 104, No. 9, Hoboken, NY.

Park, Jennifer et al., "The Effect of Matrix Stiffness on the Differentiation of Mesenchymal Stem Cells in Response to TGF-," Biomaterials, Elsevier Science Publishers BV., (Feb. 10, 2011), pp. 3921-3930, vol. 32, No. 16, Barking, Great Britain.

Floren, Michael et al., "Human Mesenchymal Stem Cells Cultured on Silk Hydrogels With Variable Stiffness and Growth Factor Differentiate Into Mature Smooth Muscle Cell Phenotype," Acta Biomateriala, (Nov. 24, 2015), Elsevier, vol. 31, pp. 156-166, Amsterdam, Netherlands.

Dawson, Jennifer et al, "Collagen Scaffolds With or Without the Addition of RGD Peptides Support Cardiomyogenesis After Aggregation of Mouse Embryonic Stem Cells," In Vitro Cellular & Devlopment Biology-Animal, (Sep. 23, 2011), vol. 47, No. 9 Springer-Verlag, NY.

Hsiao et al., Transplantation of Wharton's Jelly Mesenchymal Stem Cells to Improve Cardiac Function in Myocardial Infarction Rats, Journal of Biomedical Sciences, 5(16): 1-12 (2016).

Mathew et al., Cell Preservation in Reparative and Regenerative Medicine: Evolution of Individualized Solution Composition, Tissue Engineering, 10(11/12):1662-1671 (2004).

Buechler et al., Cross-tissue organization of the fibroblast lineage, Nature, 593:575—(2021).

Lecarpentier et al., Mechanical and Thermodynamic Properties of Non-Muscle Contractile Tissues: The Myofibroblast and the Molecular Motor Non-Muscle Myosin Type IIA, Int. J. Mol. Sci., 22:7738—(2021).

Li et al., Genetic Tracing Identifies Early Segregation of the Cardiomyocyte and Nonmyocyte Lineages,Circ Res. 125:343-355 (2019).

Sweeney et al., Muscle Contraction, Cold Spring Harb Perspect Biol, 10:a023200 :1-15 (2018).

Dominici et al., Position Paper Minimal criteria for defining multipotent mesenchymal stromal cells. The International Society for Cellular Therapy position statement, Cytotherapy, 8(4):315-317 (2006).

Schussler et al., Human Bone Marrow Contains Mesenchymal Stromal Stem Cells That Differentiate In Vitro into Contractile Myofibroblasts Controlling T Lymphocyte Proliferation, Stem Cells International vol. Article ID 6134787, 15 pages (2018).

Wang et al., CD44 inhibits-SMA gene expression via a novel G-actin/MRTF-mediated pathway that intersects with TGF-betaR/p38MAPK signaling in murine skin fibroblasts, J. Biol. Chem, 294(34) 12779-12794 (2019).

Zhu et al., The role of the hyaluronan receptor CD44 in mesenchymal stem cell migrati in the extracellular matrix, Epub, 24(4):928-35 (2006).

Schussler et al., Tripeptide Arg-Gly-Asp (RGD) modifies the molecular mechanical properties of the nonmuscle myosin IIA in human bone marrowderived myofibroblasts seeded in a collagen scaffold, PLOS One, pp. 1-19 (2019).

Schussler et al., Statistical Mechanics of Non-Muscle Myosin IIA in Human Bone Marrow-Derived Mesenchymal Stromal Cells Seeded in a Collagen Scaffold: A Thermodynamic Near-Equilibrium Linear System Modified by the Tripeptide Arg-Gly-Asp (RGD), Cells, 9(1510): 1-14 (2020).

* cited by examiner

MATERIAL AND METHOD FOR STORING, TRANSFERRING AND DELIVERING MESENCHYMAL STEM CELLS WHICH ARE IMMEDIATELY AVAILABLE AND FUNCTIONAL IN THE CONTEXT OF A MYOCARDIAL INFARCTION

The Sequence Listing in ASCII text file format of 11,184 bytes in size, created on Jun. 9, 2021, with the file name "2021-06-09SequenceListing_SCHUSSLER1_ST25," filed in the U.S. Patent and Trademark Office on Jun. 9, 2021, is hereby incorporated herein by reference.

TECHNICAL FIELD

The application describes a method comprising differentiating mesenchymal stem cells (MSC) to contractile cells and associating the differentiated cells with a 3D substrate in order to obtain a contractile tissue. The paracrine activity of the MSC is induced during the process. The biomaterials obtained are compatible with the storage, transfer, and delivery of MSC at low temperature. The preparations are immediately available and functional.

The application therefore provides a contractile cellular biomaterial, a method for producing this biomaterial as well as medical applications of this biomaterial. The biomaterial according the application is particularly suitable for preservation, angiogenesis, remodelling control and regeneration of myocardial tissue, particularly infarcted myocardial tissues.

Technological Background

Myocardial tissue may sustain lesions which reduce the contractility thereof. These myocardial lesions may lead the patient to heart failure. They may have different origins, for example a viral origin, a genetic origin or an ischaemic origin. The main cause of myocardial lesions is myocardial infarction. Myocardial infarction appears suddenly generally due to the obstruction or one or a plurality of coronary arteries, which are deprived of the supply of blood, and therefore of oxygen, that myocardial tissue cells need, thus resulting in necrosis of one or a plurality of areas of the myocardium. Myocardial infarction is an extremely frequent condition in industrialised countries (1/500), tending to occur in subjects over 50 years of age, with 25% severe forms.

Even when treated in a timely fashion within 2 hours, for example by reopening obstructed arteries (angioplasty), myocardial infraction generally leads to heart failure with more or less substantial loss of myocardial contractility. Secondary heart failure has a 5-year mortality of the same order as cancers with 50% mortality.

The decrease in myocardial contractility is particularly due to the loss (by necrosis) of cardiac muscle cells. It is also due to a loss of myocardial extracellular matrix as well as a loss of support cells of this extracellular matrix, particularly a loss of cardiac fibroblasts. However, this extracellular matrix and these support cells are necessary for the regeneration of cardiac muscle cells, which are adherent cells. The loss of matrix and of support cells therefore limits the regeneration possibilities of cardiac muscle cells. It further leads to remodelling of the ventricle, which needs to adapt to the new blood pressure state applied. The loss of cells and of extracellular matrix is further accompanied by an inflammatory reaction (initiated particularly by cell and cellular matrix debris). During infarction, mechanisms very rapidly come into play. Cell necrosis, extracellular matrix fragments and local cells will recruit inflammatory cells initially neutrophils at 8 hours, followed by M1 macrophages after 24 hours. Under the effect of local myofibroblasts, there will be a transformation of M1 type macrophages into regenerative, angiogenic, non-detersive M2 type macrophages. The acceleration of the presence of M2 macrophages enhances the recovery and preservation of myocardial tissue. Myofibroblasts are increasingly recognised as major participants in post-infarction response regulation.

Post-infarction myocardial tissue is therefore an ischaemic and inflammatory tissue, which has undergone cell loss and extracellular matrix loss.

The human body is theoretically capable of some recovery, myocardial regeneration, controlled by the myofibroblasts naturally generated by differentiation of local fibroblasts or those originating from bone marrow. Nevertheless, this natural transformation is not immediate: the transformation of fibroblasts into myofibroblasts takes at least one week and therefore these cells are not present at the acute stage, and the inflammatory reaction that is developed following infarction tends to result in ventricular remodelling and ventricular contractility impairment.

For the most advanced forms of heart failure, heart transplantation and/or mechanical assistance remain a possible treatment. The problem of these assistances is that the best survivals are merely a few years, they are very expensive, with high levels of anticoagulation accidents and impaired living conditions. Heart transplants are reserved for young subjects as there is a cruel shortage of grafts. It is a very burdensome procedure with a 50% 10-year survival rate and numerous complications with immunosuppressant treatments and secondary cancers, graft rejections, etc. For infarction, which is an extremely frequent and serious disease, it is therefore necessary to find a treatment that is effective, inexpensive and suitable for use for all ages.

In cases of infarction with initial cardiogenic shock, practically no progress has been made in 15 years even with early revascularisation with 50% hospital mortality and 50% mortality for survivors in the first year.

Cell therapy has indeed raised hopes for improving results in the case of infarction, but with little clinical application at the moment as the results are too disappointing even though some results in animals are promising. One of the explanations of the differences between the clinical studies and animal studies could be the higher availability of the cells for logistical reasons in an infarction context. No preparation for humans is immediately available. The therapies are carried out with delay and the cell are not used with optimal functionalities.

Cell therapies have therefore been envisaged for myocardial tissue preservation, healing and regeneration purposes. Various cell types have been tested, particularly differentiated cells (for example cardiomyocytes) and stem cells (for example mesenchymal stem cells). All the results with MSC cells, despite these being promising cells, are only accompanied by a very slight improvement in the contractile ventricular function (merely less than 5% whereas an improvement greater than 5% would be needed to obtain a gain in terms of survival in patients). In animals, it has been demonstrated that allogenic MSC administered immediately after infarction and modified with survival genes particularly AkT or Bcl2 could induce an increase in systolic contractility. A correlation has also been demonstrated between the initial graft take rate of the cells and recovery. The cells must be applied very early. One of the reported modes of action of MSC in vivo is the initial macrophage M1 detersive cells to M2 type regenerative angiogenic macrophages. If MSC are administered too late, the effect thereof is reduced.

Differentiated cells, such as cardiomyocytes, pose the problem of difficulty obtaining adult cells in sufficient quantity. Therefore, choices are more focused on stem cells such as mesenchymal stem cells.

In the cell therapies according to the prior art, it is frequently observed that there is insufficient survival of the cells administered, and that the graft take rate of these cells on the infarcted area is very limited with 90% loss after merely 1 hour (this factor being exacerbated further if the myocardium contracts), such that the cells administered may migrate to sites which have no connection with the area or the tissue to be treated.

Collagen patches have been used to limit the migration of stem cells, particularly of mesenchymal stem cells. Some of these patches have resulted in a limitation of ventricular remodelling with, for example, a limitation of diastolic distension, but these patches do not result in an improvement of myocardial contractility, particular of systolic ventricular contractility (cf. Simpson et al., 2007 Stem Cells 25(9): 2350-2357; more particularly table 1 of this publication).

The problem of survival, viability and graft take of the cells administered in all the more complex as the area to be treated is an ischaemic and inflammatory area, i.e. not favourable for cell survival and viability.

The logistics for transferring cells requires having at least a time-frame of 5-7 days for transport and delivery. Transferring the cells at a temperature 37° C. requires having portable incubators, $CO_2$ and oxygen, the ability to culture these cells on arrival under cGMP conditions and accredited centres. Moreover, MSC are adherent cells which will either cake together, or adhere to the walls of the transfer container. The delivery of these cells is therefore technically problematic. At 37° C., the metabolism of the cells is elevated. MSC are multipotent cells which will be differentiated anarchically. If the cells are preserved at 37° C., there is no possibility of controlling this differentiation. In terms of metabolic demand, due to the contractile properties thereof, contractile tissues compared to non-contractile tissues at ambient temperature have particularly high demands for nutrients and oxygen.

The cell therapies according to the prior art generally use cells which are stored by freezing. As cited in the study by Marquez-Curtis et al. (review Cryobiology. 2015 October; 71 (2):181-97), "the fields of tissue engineering, gene therapy, regenerative medicine and cell transplantation rely to a great degree on the ability to preserve, store and transport these cells". For logistical reasons with MSC, it is indicated that the question is not that of whether they need to be frozen as there is no other solution, but how to preserve the functionality thereof after freezing. Freezing is therefore considered as essential with current techniques. Mesenchymal cells are cells found in low numbers in tissues and which therefore need to be amplified in vitro in 2D culture. During expansion phases, the cells are subcultured using enzyme solutions. When a sufficient MSC batch is amplified, the MSC are then stored. A test batch for viral safety purposes (possible genetic mutation) is produced. Freezing also makes it possible to keep the MSC in a given differentiation state (for storing the MSC and delivering them to the centres). After thawing, in culture the cells will take several days to recover the functionality thereof (at least 72 hours). These MSC are not immediately available in an infarction context and require expertise and accreditation of the centre capable of re-expanding these cells. These skills block the use of these cells.

These cells therefore need to be thawed before being administered to the patient. The thawing step delays the patient's therapeutic care accordingly. Furthermore, regardless of the cryopreservation technique used, freezing and thawing reduce cell viability. For example, freezing and thawing of mesenchymal stem cells are accompanied by a high cellular mortality, an ultrastructural anomaly of the cells, non-adherence of the cells for more than 24 hours and a loss of paracrine immunosuppressant capacity of these cells for 48 to 72 hours after thawing. A loss of immunomodulatory paracrine activity has even been observed after thawing (Moll et al. 2014 Stem Cells 32(9): 2430-2442). As a general rule, freezing and thawing adherent cells, whether these are mesenchymal stem cells or contractile cells, impairs the adherence capacity of these cells or delays the return of the cellular adherence capacity thereof. Recovery of the cells requires culturing the cells in an incubator. The cells after thawing not being adherent, if they are injected with a substrate, they will not adhere to the substrate and the initial cell loss would be very significant. The adherence of the cells to the contractility substrate and the engagement of the cells in contractility interactions (with increase and improvement of cell/cell and cell/substrate interactions) enables better initial retention of the cells in the area to be treated unlike free cell injection which is accompanied by 90% loss of the cells after merely 1 hour and even more in a beating heart. The approach proposed in the application makes it possible to optimise cell therapy performances by better initial retention of the cells and by better preservation of the cellular contingent (better initial retention, better survival, lower secondary migration). It also makes it possible to apply cells in contact with, and not in, the infarcted area, which makes it possible to preserve the pro-regenerative immunosuppressant paracrine phenotype of the cells and preserve the differentiation state thereof.

One approach to deliver MSC could be that of culturing MSC in hypothermic 2D culture to slow down the metabolism thereof. Nevertheless, for low temperatures less than 10° C. in conventional culture medium with serum, 90% of MSC or contractile cells are already dead after merely 24 hours (Mathew et al, Tissue Eng. 2004; 10 (11-12):1662-1671). At low temperatures>0° C., there are modifications of the ATP production cycle, degradation of membrane transporters (responsible for ion modifications with increase in intracellular calcium, loss of intracellular potassium and increase in sodium, acidosis with cytoplasmic pH at normally at 7). At low temperatures, the modification of the viscoelastic properties of the membranes results in more rigid membranes. Cell damage cascades come into play with the release of intracytoplasmic enzymes, calcium-dependent phospholipase activation, apoptotic cell death pathway activation and destruction of the intracellular matrix involved in contractility phenomena (Baust et al., Organogenesis. 2009; 5 (3):90-96). What is remarkable in our invention is that in conventional culture medium with serum, we are capable of preserving the cells for more than one week without loss of this contractility.

Lactobionate-enriched hypothermic solutions have been proposed to replace chlorine and reduce the intracellular concentration thereof to limit the oncotic pressure of sucrose lactobionate and mannitol type solution. The solutions are also buffered with Hepes.

HYPERTHERMOSOL® type hypothermic solutions have been tested with progenitor cells for cardiomyocytes. In these solutions, besides the lower survival over time particularly after 4 days and over 50% mortality after 1 week (Van Buskirk et al., Bioprocess International. 2004:42-48), there is a very significant decrease in alpha-actinin after 48 hours (Herias, Cryotherapy, 16(4), S38). Therefore is moreover a very significant decrease of the marker CD9 (Ginis et al., Tissue Eng Part C Methods. 2013; 18 (6):453-463) which is a fibroblast marker. During the heating phases, the medium is toxic for the cells with the release of free radicals. It is therefore necessary to replace the medium upon heating, centrifuge the cells and use an incubator to regenerate the cells. After heating, replacing the medium and culture in an incubator, 24 to 48 hours are needed for the surviving cells to produce beats (Snyder et al., 2005, Cell Preservation Technology, 3(1), 61-74).

Therefore, these approaches are not suitable for obtaining preparations at more than 5 days, whereas at least 7 days are required for logistic concerns to transfer the preparations. If it is supposed that these preparations will be used for an unpredictable event, it is necessary to have additional shelf-life capability which the preceding approaches permit even less.

As a result, in practice, in this case in clinical practice, cell therapies intended for infarcted myocardial tissue healing or regeneration have a poor benefit-risk ratio.

In the application, the device is immediately available. There is no need to raise the temperature to 37° C. At ambient temperature, the device is contractile. The cells in the contractility substrates may optionally be used with hypothermic solutions. In this case, as the cells are already adherent to the substrate, the cells and the substrate may be washed merely by replacing the medium. In the contractility substrate, the interactions among the cells and between the cells and the substrate induce physiological Akt survival gene activation and stress proteins are lowered. This could explain the resistance of the cells in this structure under hypothermic conditions.

The application proposes myocardial tissue regeneration (or healing) therapy means, particular for infarcted myocardial tissue, which have advantages with respect to the means of the prior art, and particularly the advantage of not requiring storage in frozen form of the cells intended to be administered to the patient or subject. The means according to the application may particularly result not only in limiting or preventing remodelling of the myocardium, but also to an improvement in myocardial contractility.

SUMMARY

The application describes a biomaterial, a method for producing this biomaterial as well as medical applications of this biomaterial.

The biomaterial according to the application is contractile and the contractility thereof is spontaneous or triggered. Furthermore, it may have an inducible paracrine activity (particularly a T-cell immunosuppression paracrine activity).

The biomaterial according to the application is particularly suitable for repairing (or healing) myocardial tissue, particularly infarcted myocardial tissue.

The biomaterial according to the application may particularly promote myocardial regeneration and/or promote angiogenesis in the infarcted area. The biomaterial according to the invention may reduce the size of the infarcted area and/or limit or prevent ventricular remodelling.

Particularly notably, the biomaterial according to the application may result in a lower reduction or improvement of myocardial contractility.

Particularly advantageously, the biomaterial according to the application does not need to be frozen to be stored: it may be stored at a temperature greater than 0° C. without for all that losing the contractility (and optionally paracrine activity) properties thereof.

The biomaterial according to the application comprises a compliant three-dimensional substrate, which promotes survival and differentiation of stem cells into contractile cells and which enables contractile tissue formation. The substrate may be a solid substrate, and the cellular colonisation of the substrate may be promoted by a porous structure.

The contractile tissue is formed by the differentiation of stem cells, particularly of mesenchymal stem cells. The mesenchymal stem cells according to the application also include preparations containing MSC such as cardiosphere type "clusters" prepared from cardiac tissue fragments and enriched with progenitors for CKIT+ and MSC.

The contractile tissue may, for example comprise or consist of cells chosen from myofibroblasts, fibroblasts, myocytes, cardiomyocytes and muscle cells (including mixtures of two, three, four or five of these cell types) and progenitors for these cells and cells capable of being differentiated to these cells.

The differentiation of the stem cells, particularly mesenchymal stem cells, may particularly comprise contacting these cells with at least one agent chosen from TGF beta (including TGF beta 1), CTGF, EGF and NUX1, mechanical stress, or electrical stimulation.

A paracrine activity of the contractile tissue may be induced by contacting cells of this tissue with at least one agent chosen from IFN gamma, TNF alpha and IL1 beta and/or by applying transient hypoxia to these cells.

The (optionally porous solid) substrate may have a compliance of 0.1 to 30 $kPa^{-1}$. For example, the contractility substrates without cells may have a compliance of 0.4 $kPa^{-1}$ and of 1.5 $kPa^{-1}$ after cell colonisation.

BRIEF DESCRIPTION OF THE FIGURES

FIG. 3A; case of a biomaterial with a collagen matrix crosslinked using DHT and with RGD peptide molecules, subject to tetanic electrical stimulation and with inhibition of relaxation by RISORDAN. FIG. 3B: case of a biomaterial with a collagen matrix crosslinked using DHT, subject to 0.05 M KCl stimulation, and with BDM inhibition (cf. example 2 hereinafter).

DETAILED DESCRIPTION

Figure 1:
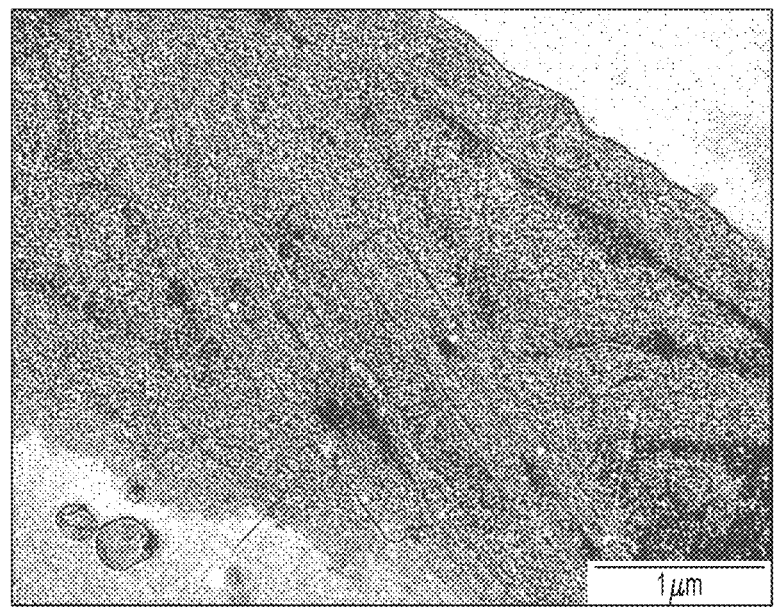
FIG. 1 shows an electron microscope view of a biomaterial according to the application (crosslinked collagen matrix by way of porous solid substrate and MSC differentiated by contact with platelet lysate; cf. example 1 hereinafter). The rectangles outlined delimit the identifiable zones of contractile filament proteins. The arrows show a regular interruption of these filaments by dense bodies or possibly a sarcomere. The biomaterial is therefore organised in a contractile structure. To our knowledge, stress bands and a terminal organisation of the contractile apparatus have never been demonstrated with MSC placed in standard 2D culture.

The application relates to a contractile biomaterial, more particularly to a contractile cellular (bio)material.

This biomaterial is particularly suitable for myocardial tissue regeneration (or healing) therapy, more particularly to a regeneration (or healing) therapy applied to an ischaemic or inflammatory myocardial tissue, more particularly post-infarction myofibroblast healing.

The means according to the application may particularly
   limit or event prevent ventricular remodelling; and/or
   reduce the size of the myocardial infarction or promote myocardial regeneration; and/or
   promote or increase angiogenesis in the infarcted area.

Particularly notably, the means according to the application may result in an improvement of myocardial contractility.

The biomaterial comprises cells and a substrate, which is a contractility substrate. Said substrate is advantageously a three-dimensional substrate. The substrate may be a solid substrate, particularly a porous solid substrate, more particularly a three-dimensional porous solid substrate.

Said substrate may for example be a sponge (for example a sponge crosslinked using DHT) or a foam. Said substrate may, for example, be a gel or a hydrogel.

The substrate may be associated with an agent.

The substrate may be physically stimulated.

The substrate may be suitable for being injected or administered by a mini-invasive route. It may have a shape memory. It may be obtained by 3D printing. The substrate may be crosslinked chemically, physically, or enzymatically. The substrate may be oriented.

The substrate may for example be a collagen-based substrate (optionally naturally, optionally purified collagen), optionally chemically modified by chemical treatment, heat treatment, or by gelatin treatment. The substrate may be modified with covalently bonded adhesion molecules.

The cells are obtained by stem cell differentiation. They form a cellular tissue and are present inside the (porous) molecular structure of the (solid) substrate, i.e. in the pores of the (porous solid) substrate. The substrate, more particularly the optionally porous solid substrate, may therefore be perceived as a 3D substrate (as opposed to conventional cell culture, which is a 2D culture).

The biomaterial is contractile, i.e. it has contraction and relaxation properties. Indeed, the cell tissue which is produced by stem cell differentiation is contractile, and the (porous) (solid) substrate containing this cellular tissue has a compliance enabling this contractility to be expressed.

Advantageously, the biomaterial (i.e. the cell tissue contained therein) further has an inducible paracrine activity.

The inducible or induced paracrine activity particularly comprises an immunomodulation activity, particularly a T-cell immunosuppression activity.

Remarkably, the biomaterial may be stored non-frozen. Indeed, it may be stored at a temperature greater than 0° C. and retain the contractility properties thereof. For example, it still displays contractility, and optionally inducible paracrine activity, properties, after storage for 5 days at a temperature greater than 0° C. but less than 10° C.

The biomaterial according to the application therefore does not require freezing and, for this reason, may therefore be very rapidly available and functional: on coming out of the storage container thereof, the biomaterial according to the application is actually immediately suitable for administration or transplantation. The subject or patient may receive same without a thawing delay, replacement of medium, or culture. It may even be used at ambient temperature, not necessarily at 37° C. The cells being adherent to the substrate and the substrate having a high porosity, there is free diffusion of the media through the substrate which will enable medium replacement without needing to carry out iterative centrifugations to recover suspended cells normally.

When placed on an ischaemic and inflammatory myocardial tissue, the biomaterial according to the application acts as a healing dressing. It promotes myocardial regeneration therein. It may also promote angiogenesis therein.

The biomaterial according to the application makes it possible to limit or even prevent post-infarction ventricular remodelling. It may further reduce the size of the infarcted area. The biomaterial may optionally prepare the ventricle for cell therapy, or other therapy aimed at treating an impaired myocardium. Several biomaterials may be used simultaneously or over time. The biomaterials may be stacked or used in "sandwich" form. They may be applied in an extracardiac site before being applied in free form or in a vascularised graft on the infarcted area. One of the sites may be the peritoneal cavity with particularly the epiploon, muscles. The biomaterial may be covered or protected on the myocardium by a device or optionally a pericardial patch.

Particularly notably, the biomaterial according to the application may result in preservation or improvement of myocardial contractility.

The application describes a method for producing this biomaterial.

The method according to the application comprises inducing the differentiation of stem cells into contractile cells, more particularly into cells which form (with one another) (and with the substrate) a contractile tissue.

The method according to the application may comprise inducing the differentiation of stem cells into contractile cells preferentially in the three-dimensional contractility substrate which will aid this differentiation. This contractility substrate with a defined compliance will make it possible to develop a contractile tissue with the onset of force and shortening of the structure formed. This contractility may be spontaneous or triggered. It may not be permanent. To obtain a contractile tissue, it is important that the cells in the substrate are contractile or have the ability to become so. These contractile cells must be connected with one another and with the substrate. The monomers/polymers of the substrate may be connected. The compliance of the substrate must not be zero. It must be compatible with deformation of the associated cellular contingent. It does not consist of an emulsion where the cellular and contractile elements are not connected and the compliance is zero. If the compliance is too high, cartilaginous bone tissue will be produced. If the compliance is too low, contractile tissue will not be obtained (and the fibroblasts for example will not be differentiated into myofibroblasts).

The stem cells may be multipotent and/or pluripotent stem cells, particularly adult (non-embryonic) stem cells, particularly cardiac stem cells (CSCs) or mesenchymal stem cells, more particularly mesenchymal stem cells. They consist more particularly of human cells. The cells may optionally be genetically modified. The stem cells may originate from the genetic reprogramming of differentiated cells. The cells may be induced pluripotent cells ("IPS"). The stem cells may originate from cell banks suitable for clinical use. The cells may be produced in cell cluster form. The cells may be fused.

Mesenchymal stem cells are frequently derived from the mesoderm and also from trans-differentiation of the endothelium or epithelium to the mesenchyme.

The stem cells, particularly mesenchymal stem cells, may originate from any source deemed suitable by a person skilled in the art, for example from adipose tissue, bone marrow, support tissue of an organ, a bone, cartilage, or a muscle, cardiac tissue and derivatives.

The stem cells, particularly mesenchymal stem cells, may be autologous or heterologous. The cells may be autologous or allogenic.

They may originate from human tissue unused or removed for another reason also from tissue removed from a recently deceased person.

In the present application, unless specified otherwise, or dictated otherwise by the context, all the terms have the usual meaning thereof in the field (s) in question.

For example, the term "mesenchymal stem cells" or "mesenchymal stromal cells" (MSC) refers in general to cells as defined in Dominici et al. 2006 (Cytotherapy 8(4): 315-317), i.e. to plastic-adherent cells (after 24 hours of contact with the plastic surface of a culture dish for example), which express CD105, CD73 and CD90, which do not express CD45, CD34, CD14 (C11b), CD79a (or CD19), and HLA-DR. MSC may further be characterised in that they can be differentiated to osteoblasts, adipocytes and chondroblasts.

Inducing the differentiation of stem cells, particularly mesenchymal stem cells, to contractile cells, more particularly to cells forming a contractile tissue, may particularly comprise contacting the stem cells, particularly mesenchymal stem cells, with at least one agent promoting differentiation chosen from
  TGF beta (Tumour Growth Factor beta) (more particularly at least TGF beta 1),
  CTGF (Connective Tissue Growth Factor),
  EGF (Epidermal Growth Factor) and
  RUNX1 (Runt-related transcription factor 1),
  transcription regulators and
  mechanical stress,
  more particularly from TGF beta, CTGF, EGF and RUNX1,
  more particularly with at least TGF beta (more particularly at least TGF beta 1), and
  more particularly with at least TGF beta (more particularly at least TGF beta 1) and optionally with at least one further differentiation agent chosen from CTGF, EGF and RUNX1.

Platelet lysate is a product which contains TGF beta (more particularly TGF beta 1) and/or CTGF and/or EGF and/or RUNX1, more particularly at least TGF beta (and optionally CTGF and/or EGF and/or RUNX1), more particularly at least TGF beta 1 (and optionally CTGF and/or EGF and/or RUNX1). Inducing the differentiation of stem cells, particularly of mesenchymal stem cells, to cells forming contractile tissue may therefore comprise contacting the stem cells, particularly the mesenchymal stem cells, with (at least) platelet lysate.

The contractile cells (or cells forming the contractile tissue) may be differentiated cells, or a mixture of differentiated cells and of stem cells (said mixture comprising at least 50%, particularly at least 80%, differentiated cells).

The contractile cells (or the (differentiated) cells forming the contractile tissue) may comprise or be cells chosen from myofibroblasts, fibroblasts, myocytes, cardiomyocytes, muscle cells (including mixtures of two, three, four or five of these cell types), more particularly cells chosen from myofibroblasts and fibroblasts (including mixtures of myofibroblasts and fibroblasts). More particularly, the (differentiated) cells forming the contractile tissue may comprise or be myofibroblasts.

More particularly, contractile cells (or the (differentiated) cells forming the contractile tissue) may comprise or be contractile cells.

The method further comprises the production of a (porous) (solid) substrate which contains this contractile tissue and enables the development of contractility. The expression "a (porous) (solid) substrate which contains a contractile tissue" means that all or part of a contractile tissue is found inside the (porous) (solid) substrate, more particularly in the pores of the (porous) (solid) substrate. The cells in the (porous) substrate will adhere to the walls of the structure and also stack of cells, the connected whole will enable effective contractile synchronous activity.

The stem cells, particularly the mesenchymal stem cells, have an inducible paracrine activity. The contractile tissue obtained in the compliant substrate comprises cells which are differentiated (generally, at least 80% of the stem cells, particularly the mesenchymal stem cells, are differentiated).

However, remarkably, the contractile tissue obtained with the (solid) substrate still has a paracrine activity which is inducible and even amplified with the appearance of specific factors whereas the cells are no longer in 2D but 3D culture, and the cells are mostly differentiated into contractile cells.

This inducible or induced paracrine activity comprises an immunomodulation, particularly immunosuppression, more particularly T-cell immunosuppression, (paracrine) activity. The immunosuppressant activity of MSC on T lymphocytes is not due to direct contact between the MSC and T lymphocytes. The immunosuppressant function of MSC involves the activation of indoleamine 2,3-dioxygenase (IDO) which will induce consumption of the tryptophan of the culture medium which is mainly responsible for the antiproliferation effect on T lymphocytes. This activation will also be accompanied by the synthesis of very numerous growth factors which will be released into the medium. The factors released are for example epidermal growth factor (EGF), platelet-derived growth factor (PDGF), vascular endothelial growth factor (VEGF), transforming growth factor (TGF beta), hepatocyte growth factor (HGF), insulin growth factor such as IGF1, angiopoietin 1 (Ang1), keratinocyte growth factor (KGF), stroma-derived factor 1 (SDF1), Follistatin-like protein 1/TSC36 (FSTL1), interleukin 10 (Il-10), PGE2, metalloproteases and regulators such as MMP2, MMP9, T1MP1, T1MP2. The majority of these cytokines have the secretions thereof amplified in the compliant 3D structure. The contractility substrate increases IL-1 and TGF beta signalling. IL-1 is the first mediator activated in post-infarction inflammation and is responsible for the initial recruitment of neutrophil inflammatory cells in the very first hours. Numerous immunomodulatory factors are also released by the activated MSC such as IDO, semaphorin-3A, B7-H4, LIF, TSG6, galectin, HO-1, 11-6, 11-10, TGF beta, PGE2, PD-L1/2. Certain paracrine factors released require a 3D structure with compliance such as TSG6 and CXCR4. TSG6 is known to have an important role in infarction. In compliant 3D substrates, PGE2 production is particularly increased. The activation of the cells in substrate by interferon gamma will increase the synthesis of TGF beta, PGE2, BMP2, factor H (complement inhibitor), Gal9. Factor H is very important as in the infarcted area, there is a large amount of complement which will result in local cell lysis. Factor H will therefore protect the cells from complement-induced lysis and therefore improve the survival thereof. Thawed cells have a decrease in factor H and therefore are particularly sensitive to complement-induced lysis. The preparation according to the application is therefore very superior. IL-10 is known to reduce the post-infarction inflammatory response. IDO and PGE2 promote the transformation of M1 type macrophages to M2 type macrophages post-infarction. As regards the lysis of non-denatured natural collagen, MSC in 2D culture cannot lyse collagen as MMP14, MMP1, MMP8 or MMP13 activities are not present. MMP14 activity is a membrane metalloproteinase which remains confined to the cell. As the MSC remain in the substrate, this activity will therefore remain contained in the substrate. MMP14 activity may make it possible to effectively lyse natural collagen which is particularly over-represented post-infarction in the slough area. MMP14 activity also makes it possible to modify the activities of soluble MMP2 and MMP9 metalloproteinases which, once activated, will be capable of lysing natural collagen. These factors may then modify the surrounding natural collagen.

It has been demonstrated that the paracrine factors released by the immunosuppressant in vitro MSC are factors which will promote tissue regeneration in vivo. The paracrine factors released by the immunosuppressant MSC will for example accelerate the transformation of M1 macrophages to M2 type macrophages in infarction.

These factors may be optionally released in vesicles or in more complex membranous structures such as "exosomes".

The inducible or induced paracrine activity may thus comprise a T lymphocyte proliferation inhibition (paracrine) activity.

More particularly, the inducible or induced paracrine activity is a (paracrine) activity which promotes immunomodulation (particularly immunosuppression) and which promotes cell generation and/or angiogenesis. More particularly, the inducible or induced paracrine activity is a (paracrine) activity which promotes T-cell immunosuppression.

The method according to the application may therefore further comprise inducing a paracrine activity of said contractile cells (or of said contractile tissue, i.e. inducing a paracrine activity in cells of this contractile tissue).

Inducing a paracrine activity of said contractile cells (or of cells of said contractile tissue) may particularly comprise:
contacting cells of these contractile cells (or of this contractile tissue) with at least one paracrine activity induction agent chosen from
IFN gamma (interferon gamma),
TNF alpha (Tumour Necrosis Factor alpha) and
IL1 beta (interleukin 1 beta),
more particularly with at least IFN gamma,
more particularly with INF gamma and optionally at least one further differentiation induction agent chosen from TNF alpha and IL1 beta, and/or applying transient hypoxia to said contractile cells (or to cells of said contractile tissue), for example a hypoxia less than 5% for 1 or 2 days.

Contacting with IFN gamma may for example be carried out at a rate of more than 10 IU/ml, more particularly from 50 to 1000 IU/ml, more particularly from 50 to 500 IU/ml of IFN gamma. Alternatively or additionally to the induction of a paracrine activity of the contractile tissue, the method according to the application may comprise the induction of a paracrine activity on the stem cells, particularly on the mesenchymal stem cells, before they are differentiated to cells forming a contractile tissue. Thus, before inducing the differentiation of the stem cells, more particularly of the mesenchymal stem cells, to contractile cells, more particularly to cells forming a contractile tissue, the method according to the application may comprise (alternatively or additionally to the induction of a paracrine activity of the contractile tissue):

contacting said stem cells, more particularly said mesenchymal cells, with at least one paracrine activity induction agent chosen from IFN gamma (interferon gamma), TNF alpha (Tumour Necrosis Factor alpha) and IL1 beta (interleukin 1 beta), more particularly with at least IFN gamma, more particularly with INF gamma and optionally at least one further differentiation induction agent chosen from TNF alpha and IL1 beta, and/or applying transient hypoxia to said stem cells, more particularly said mesenchymal cells (for example a hypoxia less than 5% for 1 or 2 days).

Alternatively or additionally to being porous, the (solid) substrate used may advantageously have a compliance of 0.1 to 30 $kPa^{-1}$, more particularly of 0.4 $kPa^{-1}$ to 20 $kPa^{-1}$, more particularly of 0.5 to 15 $kPa^{-1}$, more particularly of 0.5 to 5 $kPa^{-1}$ (compliance of the (porous) solid substrate with or without cells, more particularly without cells).

The compliance of the substrate may be obtained after cell colonisation and crosslinking. Cell colonisation and crosslinking increase the compliance of the substrate.

According to materials science, compliance is a quantity characterising the elastic behaviour of a material. A compliance is defined as the inverse of a modulus of elasticity, and is expressed in $Pa^{-1}$. Schematically, compliance may be viewed as the degree to which a container can sustain a pressure or force without rupturing.

The method according to the application may thus be defined as being a method for producing a contractile cellular biomaterial, characterised in that the method comprises:

inducing the differentiation of multipotent mesenchymal stem cells to contractile cells in a contractility substrate which is a (three-dimensional) (solid) substrate, and inducing a paracrine activity of said contractile cells, the induced paracrine activity further comprising a T-cell immunosuppression and/or indoleamine 2,3-dioxygenase (IDO) activation activity, said method being further characterised in that inducing the differentiation of multipotent mesenchymal stem cells to contractile cells comprises contacting the mesenchymal stem cells with at least one agent promoting differentiation chosen from TGF beta, CTGF, EGF, NUX1, transcription regulators and mechanical stress and electrical stimulation, more particularly from TGF beta, CTGF, EGF and NUX1, said three-dimensional (solid) substrate has a compliance of 0.1 to 30 $kPa^{-1}$, and inducing a paracrine activity of said contractile cells comprises contacting these contractile cells with at least one paracrine activity induction agent chosen from IFN gamma, TNF alpha and IL1 beta, and/or applying transient hypoxia to cells of this contractile tissue, the (solid) contractility substrate containing the contractile cells produced being a contractile cellular biomaterial suitable for myocardial tissue regeneration therapy.

More particularly, the method according to the application may thus be defined as being a method for producing a contractile cellular (bio)material suitable for myocardial tissue regeneration therapy, which comprises:

inducing the differentiation of mesenchymal stem cells to contractile cells and producing a (porous) solid substrate which contains these contractile cells, and inducing a paracrine activity in these contractile cells, the induced paracrine activity comprising a T-cell immunosuppression activity, said method being further characterised in that inducing the differentiation of the mesenchymal stem cells to contractile cells comprises contacting the mesenchymal stem cells with at least one agent promoting differentiation chosen from TGF beta (more particularly with at least TGF beta 1), CTGF, EGF and RUNX1, more particularly with at least TGF beta (more particularly with at least TGF beta 1), and optionally at least one further agent promoting differentiation chosen from CTGF, EGF, RUNX1, transcription regulators and mechanical stress, more particularly from CTGF, EGF and RUNX1, the contractile cells comprise or are cells chosen from myofibroblasts, fibroblasts, myocytes, cardiomyocytes, muscle cells (including mixtures of two, three, four or five of these cell types), more particularly comprise or are cells chosen from myofibroblasts and fibroblasts, more particularly comprise or are myofibroblasts, said (porous) (solid) substrate has a compliance of 0.1 to 30 $kPa^{-1}$, and inducing a paracrine activity in the contractile cells comprises contacting these contractile cells with at least one paracrine activity induction agent chosen from IFN gamma, TNF alpha and IL1 beta, more particularly with at least IFN gamma and optionally with at least one further paracrine activity induction agent chosen from TNF alpha and IL1 beta, and/or applying transient hypoxia to these contractile cells.

More particularly, the method according to the application may thus be defined as being a method for producing a contractile cellular (bio)material suitable for post-infarction myocardial tissue regeneration therapy, and in that the contractile cells are chosen from myofibroblasts, fibroblasts, myocytes, cardiomyocytes and muscle cells and progenitors of these cells, and the cells capable of being differentiated to these cells.

More particularly, said method is characterised in that:

inducing the differentiation of the mesenchymal stem cells to contractile cells comprises contacting the mesenchymal stem cells with TGF beta, more particularly with TGF beta 1, and inducing a paracrine activity of said contractile cells comprises contacting the cells of this tissue with IFN gamma.

Advantageously, the contractile cells form a contractile tissue in the (porous) (solid) substrate.

The (porous) (solid) substrate containing the contractile tissue produced is a contractile cellular biomaterial suitable for tissue regeneration therapy, particularly of human tissue, such as muscle tissue, non-contractile human tissue, cardiac tissue, more particularly human myocardial tissue.

More particularly, the method according to the application may be defined as being a method for producing a contractile cellular (bio)material suitable for myocardial tissue regeneration therapy, which comprises inducing the differentiation of mesenchymal stem cells into contractile cells which in the compliant substrate will form a contractile structure (particularly a contractile tissue), and inducing a paracrine activity in these contractile cells, the induced paracrine activity comprising a T-cell immunosuppression activity, said method being further characterised in that inducing the differentiation of the mesenchymal stem cells into contractile cells comprises contacting the mesenchymal stem cells with (at least) TGF beta, more particularly with (at least) TGF beta 1 (and optionally at least one further agent promoting differentiation chosen from CTGF, EGF and RUNX1), the contractile cells comprise or are cells chosen from myofibroblasts, fibroblasts, myocytes, cardiomyocytes, muscle cells and progenitors thereof, a stem cell preparation containing mesenchymal cells, such as "cardiospheres" for example, for these cells (including mixtures of two, three, four or five of these cell types), more particularly comprise or are cells chosen from myofibroblasts and fibroblasts, more particularly comprise or are myofibroblasts, said (porous) (solid) substrate has a compliance of 0.1 to 30 $kPa^{-1}$, and inducing a paracrine activity in these cells comprises contacting these contractile cells with (at least) IFN gamma (and optionally with at least one further paracrine activity induction agent chosen from TNF alpha and IL1 beta).

According to an advantageous embodiment, the stem cells (particularly the mesenchymal stem cells) are placed or implanted in the (porous) (solid) substrate (particularly in the pores of this (porous) (solid) substrate)) before inducing the differentiation thereof into cells forming a contractile tissue. All the stem cells (particularly all the mesenchymal stem cells), or at least 50% thereof or at least 60% thereof or at least 80% thereof, may be placed or implanted (or contained) within the porous (molecular) structure of the (solid) substrate.

The method according to the application may then comprise placing or implanting (mesenchymal) stem cells into the (porous) (solid) substrate (more particularly in the pores of the (porous) (solid) substrate), then inducing the differentiation of these (mesenchymal) stem cells to cells forming a contractile tissue.

The induction of the differentiation of (mesenchymal) stem cells to cells forming a contractile tissue and the production of a (porous) (solid) substrate which contains this contractile tissue may thus be carried out:

by producing a (porous) (solid) substrate wherein (in the pores whereof) (mesenchymal) stem cells are contained and by inducing the differentiation of all or part (at least 50%, more particularly at least 80%) of these (mesenchymal) stem cells to cells which form a contractile tissue (inside the porous structure of the (solid) substrate).

The cells which form the contractile tissue may particularly be bonded together by intercellular junctions. The intercellular junctions may particularly be or comprise connexin intercellular junctions (i.e. intercellular junctions wherein the junction proteins comprise one or more connexins). The intercellular junctions may more particularly be or comprise communicating intercellular junctions, more particularly connexon communicating intercellular junctions.

The contractile tissue is, or is found, fixed to the substrate. Advantageously, said contractile tissue is bonded to the (porous) (solid) substrate, for example by anchoring junctions. The anchoring junctions may particularly be anchoring molecules. The anchoring molecules may particularly comprise anchoring proteins, more particularly at least one transmembrane protein connected to the cytoskeleton and to the contractile apparatus of the cell. The anchoring junctions may particularly be anchoring molecules, which comprise at least one integrin which are mechanoreceptors and therefore will make it possible to determine the compliance of the substrate. Stimulation of the receptors will induce an increase in the connections of the cells with one another and also improve the survival of the cells and promote differentiation to contractile cells and an organisation of the contractile apparatus according to the location of this interaction by also reinforcing same.

More particularly, the method according to the invention is characterised in that the contractile cells form a contractile tissue, and in that this contractile tissue is bonded to the contractility substrate by anchoring molecules which comprise at least one integrin.

The differentiation of the stem cells, particularly the mesenchymal stem cells, to cells forming a contractile tissue may be induced until detection of a cellular differentiation marker, said cellular marker being for example chosen from alphaSMA (alphaSmoothMuscleActin) and mysosin (more particularly mysosin type II). Said cellular marker is more particularly alphaSMA. The contractile tissue then contains cells which have at least the marker alphaSMA, more particularly the marker alphaSMA and myosin (more particularly mysosin type II). At the level of the contractile cells in the contractility substrates, alphaSMA will be associated with the contractility bands per se with regard to the integrin surface interaction.

The cells forming a contractile tissue may be or comprise myofibroblasts, fibroblasts, myocytes, cardiomyocytes, muscle cells (particularly skeletal muscle cells, smooth muscle cells or striated muscle cells). The cells forming a contractile tissue may be a mixture of a plurality of these cell types, for example a mixture of at least two or at least three cell types chosen from myofibroblasts, fibroblasts, myocytes, cardiomyocytes and muscle cells, for example a mixture of myofibroblasts and fibroblasts.

The cells may be associated with further contractile or non-contractile cells such as endothelial cells. Generally, any cells present in the core may be associated.

More particularly, the cells forming a contractile tissue may be or comprise myofibroblasts which express the marker alphaSMA.

The contractile tissue is essentially formed of differentiated cells: generally, at least 80% of the cells forming same are differentiated cells (which may for example express the myofibroblast marker alphaSMA). However, the cells which form the contractile tissue still express certain cellular markers which are usually observed on (mesenchymal) stem cells, and not on differentiated cells (which in this instance may also express the marker alphaSMA and/or myosin).

For example, the contractile tissue may comprise cells which are positive for one or a plurality of the markers CD105, CD54, CD73, CD105 and CD90, more particularly for one or a plurality of the markers CD105, CD54, CD73 and CD105.

For example, the contractile tissue may comprise cells which are negative for one or a plurality of the markers CD45, HLA-DR, CD14, CD19, CD34 and CD106, more particularly for one or a plurality of the markers CD45 and HLA-DR.

The contractile tissue may particularly comprise cells which are positive for one or a plurality of the markers CD105, CD54, CD73 and CD105, and which are negative for one or a plurality of the markers CD45 and HLA-DR.

The contractile tissue may for example comprise cells which are positive for the markers CD105, CD54, CD73 and CD105, and which are negative for the markers CD45 and HLA-DR. Thus, the contractile tissue may comprise cells which are positive for the marker alphaSMA (and optionally positive for myosin), positive for the markers CD105, CD54, CD73 and CD105, and negative for the markers CD45 and HLA-DR.

Alternatively or additionally, the differentiation of the stem cells, particularly of the mesenchymal stem cells, to cells forming a contractile tissue may be induced until activation of the canonical Wnt signalling pathway. The activation of the canonical Wnt signalling pathway may cause accumulation of beta-catenin in the cytoplasm and the translocation thereof to the nucleus to act as a transcription factor transcriptional co-activator.

Surprisingly, the contractile tissue retained an inducible paracrine activity (particularly an inducible paracrine activity promoting T-cell immunosuppression). Having an inducible paracrine activity, particularly an inducible paracrine immunosuppressant activity, is particularly advantageous for the targeted medical applications (immune rejection risk control and reduction).

The induction of this paracrine activity may result in:
an activation or stimulation of IDO (inducible indoleamine 2,3-dioxygenase) and/or in
an increase in the expression of certain proteins, particularly certain metalloproteinases, such as MMP2, MMP9 and MMP14, and/or in
an increase in the expression of one or a plurality of the molecules chosen from
TSG6 (tumour necrosis factor inducible gene 6),
VEGF (Vascular endothelial growth factor),
PDGF (Platelet-Derived Growth Factor),
angiopoietin, IL1 (Interleukin-1),
IGF1 (Insulin-Like Growth Factor-1),
FSL1 (synthetic lipoprotein Pam2CGDPKHPKSF), and
PGE2 (Prostaglandin E2).

The induction of the paracrine activity (of cells) of said contractile tissue may therefore be carried out until (in a sufficient quantity and/or time) one or a plurality of the following elements is obtained:
IDO activation or stimulation,
expression or increased expression of at least one metalloproteinase (such as MMP9 and/or MMP2 and/or MMP14),
more particularly until (in a sufficient quantity and/or time) one or a plurality of the following elements is obtained:
IDO activation or stimulation,
secretion, or increased secretion, of MMP9,
secretion, or increased secretion, of MMP2, and
(membrane) expression, or increased membrane expression of MMP14, more particularly at least until activation or stimulation of IDO and/or expression or increased expression of one or a plurality of metalloproteinases, more particularly at least until activation or stimulation of IDO and/or secretion or increased secretion of MMP9 and/or MMP2, more particularly at least until secretion or increased secretion of MMP9.

Thus, after inducing the paracrine activity, the contractile tissue may comprise cells, which express MMP9, MMP2 and MMP14, more particularly which secrete MMP9.

It was further observed that the inducible (or induced) paracrine activity may even be greater than that observed with undifferentiated stem cells. For example, the (differentiated) cells of the contractile tissue according to the application (contained in the porous solid substrate) may have a secretion of metalloproteinase(s), more particularly of MMP9 and MMP2, more particularly of MMP9, which is greater than that observed with mesenchymal stem cells (in conventional 2D culture). This feature is favourable for angiogenesis, and is therefore advantageous for the targeted medical applications, more particularly for myocardial tissue regeneration therapy in a chronic infarction context.

Thus, surprisingly, the contractile tissue comprises contractile cells which comprise cells which express the marker alphaSMA and optionally myosin, and which, after induction by TGF beta 1, secrete at least one metalloproteinase chosen from MMP9 and MMP2 and MMP14.

The compliant (porous) substrate may for example be a gel, hydrogel, a shape-memory structure. The three-dimensional substrate may be liquid phase and once delivered after activation may be converted to solid phase such as for example solution, paste, a gel, a colloidal suspension, a plasma. The substrate may be a cryogel or substrate suitable for injection with shape memory. The constituents of the substrate may be intelligent agents capable of being assembled, deformed and optionally reassembled. They consist of materials tending to assemble on a molecular level to form nano, micro or macrostructures or combinations.

The substrate may be filaments, a sponge, materials with filarial ultrastructure, alveolar sponge ultrastructure, structural analogues in the form of interface, powder, conduits, sphere, microsphere, film, micro or nanofibrils, lipidic membrane, fibres, matrixes, patches, fabrics, woven structure, beta or alpha structures involved in the formation thereof. The substrate may be composed by the association of the various substrates or of stacking of the same substrate. This may be multilayer films obtained by microfluidics for example. The substrate may be manufactured using "3D printed" type techniques.

The (porous) (solid) substrate may be a woven substrate or a non-woven substrate, more particularly a gel, a hydrogel, a foam, a sponge.

The substrate may be manufactured from monomer, polymer or combination. It may consist of natural materials or not. For natural materials, they may be optionally produced using molecular biology techniques.

The substrate may be completely, partially or not biodegradable.

The substrate may be manufactured from optionally natural polymers, monomers. Any polymers may be used, synthetic or natural or combination, provided that the substrate obtained fulfils the differentiation and contractility properties as defined above particularly in terms of compliance. However, natural polymers which have adhesion molecules will be preferred. Among natural polymers: collagen. Collagen is the natural component of the extracellular matrix in tissues and is therefore particularly suitable.

The substrate may contain or be manufactured with a natural polymer such as collagen, gelatin, a collagen-derived product, fibrinogen, fibrin, silk including FIBROIN silk which could be of particular interest due to particular adhesion molecules, alga, alginate, proteoglycans, glycoproteins, glycosaminoglycans, alginate, agarose, hyaluronic acid, agar, chitosan, fibrinogen/fibrin, carboxymethyl chitosan, sucrose octasulphate, dextran, cellulose, methyl cellulose, sepharose, protein mimicked by SEPHADEX (such as latex) or the association thereof. The properties of these polymers may optionally be modified.

The 3D substrate may be obtained from grouping different micro or nanostructure tissue substrates, filaments or tubes, sponge, powder, conduit, sphere, film, micro or nanofibrils, membrane, fibre, mesh, matrix, patch, tissue sheet, decellularised (devoid of cells) tissue, knitted tissue, wadding or combination.

The three-dimensional scaffold contains collagen which consists of collagen (I, II, III, IV, V, VI, VII, XI and other collagens), or the association of different species. The term "collagen" also denotes insoluble collagen, soluble collagen, atelocollagen prepared by removing telopeptides on the ends of the collagen molecules using a protease other than collagenase. It may consist of a synthetic collagen. This may also be recombinant synthetic gelatin. The three-dimensional collagen scaffold may also be a normal tissue of autologous, homologous or heterologous origin. This tissue may be decellularised tissue. Various protocols to decellularise tissues may be used (by osmotic shock, ionic and non-ionic detergents, proteolytic digestions, DNase/RNase treatments). Decellularisation may be coupled with techniques aiming to modify the properties of the substrate such as the porosity. The decellularised tissue could optionally be used but the problem of these tissues is the rigidity thereof. Indeed, after cell extraction, the empty spaces are compacted and rigidity increases. It also consists of non-porous tissue. The methods for increasing the porosity of these tissues render these tissues more immunogenic and lose mechanical properties of these tissues.

The collagen may be purified from tissue containing collagen: autologous, homologous or heterologous such as ureter, pericardium, tissue matrix such as the heart, submucosa such as porcine intestinal submucosa "SIS", blood vessel, tendon, fascia, optionally decellularised dermis, aponeurosis, membrane such as amniotic membrane, dura mater. This could be synthetic collagen copies such as polymer fibres or peptides forming fibrils. The collagen may be chemically modified and the product obtained by succinylation or esterification or formation of carboxyamides, or collagen deamination.

The scaffold may be manufactured from organic synthetic polymers such as poly(lactic acid) (PGA) and/or poly(DL-lactide-Co-glycolide) (PLGA) and/or poly(DL-lactide-Co-caprolactone) (PCL), a collagen derivative such as gelatin, a polypeptide obtained by collagen hydrolysis, collagen denatured by heating. Synthetic polymers bonded to the collage may be chosen from Poly(3-hydroxybutyrate) (PHB)+++, poly(e-caprolactone) (PCL), silk, poly-lactic acid (PLA), polyamide (PA), polylactic acid (PLA), polyglycolic acid (PGA), poly(L-lactic) (PLLA), PLGA, poly(anhydrides) (PA), polycarbonate (PC) hydroxy acids, polyorthoesters (POE), propylfumarates (PPF), polysaccharides, polylactone (PL), polycaprolactones, polyamides, polyamino acids, polyacetals of polyphosphazenes (PPZ), biodegradable polycyanoacrylates, biodegradable polyurethanes (central unit), polysaccharides, polypyrrole, polyanilines, polythiophene, polystyrene, polyester (PE), non-biodegradable polyurethanes, polyureas, poly(ethylene-terephthalate) (PET), poly(vinyl ethylene acetate), polypropylene, polymethacrylate, polyethylene, polycarbonates, poly ethylene oxide, poly(vinyl alcohol) (PVA), Gore-Tex (polytetrafluoroethylene), Dacron (polyethylene terephthalate), polytetrafluoroethylene (PTFE), poly-ethylene-glycol (PEG), polyglycerol sebacate (PGS), copolymers described above, with one of the additives above, and mixtures of one of the polymers, copolymers, and additives with one another and association of synthetic derivatives with biological products.

Preferentially, type I, II and III type purified collagens will be used. Certain collagens have specific adherence properties and may then be associated such as collagen IV.

The scaffold may be a sponge type matrix obtained by dehydrothermal treatment (DHT) crosslinking. The scaffold may also be a foam, via a gelatin foam. This may be a collagen form such as GELFOAM™. The DHT matrix corresponds to matrixes obtained by dehydrothermal crosslinking. The manufacture of these substrates may be accompanied by a freeze-drying step or the temperature is lowered to below zero degrees to increase the porosity of the substrate then high-temperature low-pressure crosslinking is performed to crosslink the substrate. A matrix obtained by DHT corresponds to the Bard ULTRAFOAM™ matrixes. A matrix manufactured with type I and type III collagen may be used as a haemostatic sponge. The initial collagen is soluble in a 0.5% w/w collagen solution in 0.05 M pH 3.5 acetic acid. The preparation is dried by controlled cooling to obtain sponges. The pore size and the distribution are essentially dependent on the rate of freezing (0.25-1° C./min), the final freezing temperature of (−90° C. to −5° C.). This sponge is then subjected to DHT crosslinking (105° C. for 16 hours for a pressure less than 100 mTorr) to introduce covalent bonds between the collagen chains without denaturing same of gelatin.

During the manufacture, the substrate may be oriented by adjusting for example the temperature gradient.

The collagen may be associated with glycosaminoglycans. The scaffolds may optionally be manufactured using an electrospinning technique but the problem of this approach is that the substrates have a very high compliance and there is difficulty colonising these substrates.

The substrate may be oriented. The substrates have a very high porosity close to 98%. The porosity defines the capacity of the substrate to allow liquids to pass. The substrate may have a sponge structure on an ultrastructural scale. This sponge structure will promote the initial capture of the cells with retention in the substrate. Some substrates also act as sponges with suction in the effect of the initial compression of the substrates, and retention inside the cells and liquids. In the substrate, there is initially a very significant migration of the cells which will make it possible to colonise the entire substrate rapidly in the first week. When the contractile structures are developed, this migration capacity is lost. This migration capacity may be optionally used to colonise other 3D substrates placed in contact. This approach makes it possible to produce cultures at very low cost in a 3D environment without having to make iterative cultures in 2D systems. Moreover, this 3D culture makes it possible to culture more cells in a limited space.

The substrate may advantageously have pores of intermediate size to enable nutrient diffusion, in vitro cellular colonisation, in vivo cellular colonisation.

The porosity of the porous solid substrate is adapted to the presence of contractile cells in these pores. The porosity may particularly be from 20 to 200 μm, for example from 50 to 100 μm. This porosity may be homogeneous or non-homogeneous.

The substrate may be oriented. Compliant oriented substrates promote differentiation to contractile cells. The forces developed in oriented structures are greater. There is a synergy of action between the orientation of the substrates and potential mechanical stimulation of these substrates.

The substrate may be crosslinked. Various chemical (such as for example aldehydes, isocyanates, carbodiimides), physical, biological and combination crosslinking methods exist. In physical crosslinking for example UV, dehydrothermal (DHT). For chemical crosslinking, preferably non-toxic crosslinking agents for cells such as diphenylphosphorylazide, carbodiimides, EDC (1-ethyl-3-(3-dimethylaminopropyl-carbodiimide hydrochloride), EDC/NHS EDC (1-ethyl-3-(3-dimethylaminopropyl-carbodiimide hydrochloride) in the presence of NHS (N-hydroxy-succinimide), EGS (ethylene glycol-bis (succinic acid N-hydroxysuccinimide ester), genipin may be chosen. Optionally glutaraldehyde may be used if it is detoxified. It may be possible to use citric acid as a crosslinking agent for collagen electrospinning processes for example. Enzymatic crosslinking such as for example transglutaminase may also be used. The crosslinking may take place in vivo. The substrate may be crosslinked several times in vitro and in vivo. Chemical crosslinking reduces the cell adhesion sites. We propose associating crosslinking with adhesion molecules to improve substrate functionality. We observed that it was possible to crosslink the substrate with genipin (concentration<10 mM for 24 hours at 37° C., optimal concentration 1.5 mMol for 24 hours at 37° C.) without modifying either the capability of the cells to be differentiated into contractile cells in the substrate, or the preservation of the contractility of the substrate and the inducible paracrine capacity of the cells. The crosslinking agents may influence the differentiation capacity of the cells. This is very interesting as normally the crosslinked substrates have a higher rigidity and therefore a lower contractility. We observed contractility in the DHT crosslinked substrates crosslinked with genipin or crosslinked with EDC/NHS. The cells are differentiated to myofibroblasts and the inducible paracrine activity is the same in crosslinked or non-crosslinked substrates. The contractile activity remains present in the crosslinked substrates.

The structure of the porous solid structure may be presented in the form of a three-dimensional scaffold. It may for example comprise a polymer (such as those listed above) in crosslinked form. The crosslinking of the polymer (for example collagen, particularly type I or type III collagen) may for example by performed with a chemical process, more particularly with genipin (for example genipin at 0.1-10 mM) or with 1-ethyl-3-(3-dimethylamino propyl) carbodiimide (EDC) and/or with a physical process, particularly by dehydrothermal treatment (DHT) crosslinking.

The compliant substrate may further comprise adhesion molecules, particularly adhesion peptide molecules, more particularly RGD (Arg-Gly-Asp) peptide molecules. The adhesion molecules include polynucleotides, adhesion peptides which include peptides, polypeptides, proteins or molecules capable of binding to the cell receptors promoting cell adherence with high affinities as is the case of integrin receptors and according to current bibliographic data. The adhesion peptides may be formed of optionally natural amino acids and/or analogues. One or a plurality of amino acids of the adhesion peptide may be substituted. The adhesion peptides include peptides, polypeptides or proteins or molecules (optionally of natural origin) containing the initial adhesion sequence. They may also consist of peptidomimetic structures capable of fulfilling the same function as the peptide. The terms polypeptide, peptide and protein may be used for one another. This also comprises the addition of a chemical entity such as a carbohydrate group, a phosphate group, a farnesyl group, an isofarnesyl group, a fatty acid group, a binding promoter for conjugation, functionalisation, or any other modification or organic or inorganic molecule association including polyethylene glycol (PEG) or any other synthetic molecule. These modifications may also include the cyclisation of the peptide containing the adhesion sequence. A plurality of adhesion peptides may be associated and the peptide may refer to an individual peptide or to a collection of peptide.

The molecules or the adhesion peptides may be modified and also belong to the same molecule or to a molecule serving as an intermediary for binding to the substrate.

The peptide further includes adhesion peptides aimed at interacting with the adhesion receptor per se, with the co-receptors (involved not necessarily in adhesion). Binding to these co-receptors modifies and/or the adhesion and/or the activation and/or the transduction of the receptor.

The integrins recognising natural collagen are integrins alpha 1, alpha 2, alpha 10 and alpha 11 associated with the beta 1 chain.

According to the present invention, the adhesion peptide could be advantageously the RGD peptide corresponding to arginine (R)-glycine (G)-aspartic acid (D), integrin recognition motif on fibronectin described by Pierschbacher et al. ("linear RGD" Pierschbacher M D et al., Nature. 1984, May 3-9; 309(5963):30-3), or on vitronectin as described by Plaff M. et al. ("cyclic RGD" Plaff M et al., J Biol Chem, 1994 Aug. 12; 269(32):20233-8). The "RGD motif" also includes all the peptide ligands that will interact with one of the integrin receptors, all the alphav receptors (5 receptors): $\alpha_v\beta 1$, $\alpha_v\beta 3$, $\alpha_v\beta 5$, $\alpha_v\beta 6$, $\alpha_v\beta 8$, $\alpha II_b\beta 3$, $\alpha_5\beta 1$, $\alpha 8\beta 1$. Further adhesion peptides such as PHSRN peptides or obligatory proteoglycan domain of the extracellular matrix (obligatory heparin domains) based on X-B-B-X-B-X (SEQ ID NO: 5) or X-B-B-B-X-X-B-X (SEQ ID NO: 6), order models of B-B-X-B (SEQ ID No: 7), where B is a basic amino acid and X is a hydroxy amino acid, YOGSR (SEQ ID NO: 8) (Iwamoto et al., Science. 1987 Nov. 20; 238 (4830):1132-4) and IKVAV (SEQ ID NO: 9) (-Ile-Lys-Val-Ala-Val-) (Tashiro et al., J Biol Chem. 1989 Sep. 25; 264 (27):16174-82) RYWLPR (SEQ ID NO: 10) or RNIAEIIKDI (SEQ ID NO: 11) (Liesi P et al., FEBS Letters. Volume 244, Issue 1, 13 Feb. 1989, Pages 141-148) of laminin, REDV (SEQ ID NO: 12) (Massia S P et al., J Biol Chem. 1992 Jul. 15; 267 (20): 14019), PHSRN (SEQ ID NO: 13) (-Pro-His-Ser-Arg-Asn) (Aota S et al., J Biol Chem. 1994 Oct. 7; 269 (40): 24756-61) or KNEED (SEQ ID NO: 14) (Altroff H et al., J Biol Chem. 2001 Oct. 19; 276 (42)38885-92; Wong J Y et al., Biomaterials. 2002 September; 23(18):3865-70) or EILDV (SEQ ID NO: 15) of fibronectin, obligatory proteoglycan domain of adhesion proteins such as KRSR (SEQ ID NO: 16) (Dee K C et al., J Biomed Mater Res. 1998 Jun. 5; 40(3):371-7; Rezania A et al., Biotechnol Prog. 1999 January-February; 15(1)19-32) or FHRRIKA (SEQ ID NO: 17) (Rezania A et al., Biotechnol Prog. 1999 January-February; 15 (1)19-32), sequence of VAPG (SEQ ID NO: 18) and of KQAGDV (SEQ ID NO: 19) of elastin (Mann & West et al., J Biomed Mater Res. 2002 April; 60 (1): 86-93), GFOGER of type I collagen (Ernsley J et al., Cell. 2000 March DEGA (Rabenau K E et al., Oncogene. 2004 Jun. 24; 23(29):5056-67).

In an embodiment, the substrate is modified with a molecule corresponding to fibronectin particularly to the region containing the RGD motif. At the level of fibronectin, RGD expression is linear whereas in vitronectin, the cyclic form is involved. The sequences may for example be RGD, RGDS (SEQ ID NO: 20), GRGD (SEQ ID NO: 21), RGDV (SEQ ID NO: 22), RGDT (SEQ ID NO: 23), GRGDG (SEQ ID NO: 24), GRGDS (SEQ ID NO: 1), GRGDY (SEQ ID NO: 25), GRGDF (SEQ ID NO: 26), YRGDS (SEQ ID NO: 27), YRGDDG (SEQ ID NO: 28), GRGDSP (SEQ ID NO: 29), GRGDSG (SEQ ID NO: 30), GRGDSY (SEQ ID NO: 31), GRGDVY (SEQ ID NO: 32), GRGDSPK (SEQ ID NO: 33), CGRGDSPK (SEQ ID NO: 34), CGRGDSPK (SEQ ID NO: 35), CGRGDSY (SEQ ID NO: 36), cyclo(RGDfK) (SEQ ID NO: 37), YAVTGRGD (SEQ ID NO: 38), AcCGG-NGEPRGDYRAY-NH2 (SEQ ID NO: 39), AcGCGYGRGDSPG (SEQ ID NO: 40) and RGDPASSKP (SEQ ID NO: 41), the cyclic variants of these peptides, the linear or branched multivalent variants (Dettin M et al., 2002, J. Biomed. Mater, res. 60:466-471; Monaghan S et al., 2001, Arkivoc, 2:U42-49; Thumshirn G et al. 2003, Chemistry 9:2717-25; Scott E S et al., 2001, J. Gene Med. 3:125-134), as well as the combination of two or more than two of these peptides.

In order to be effective, the adhesion peptide, if it is not included in the primary structure of the regular polymer, it must be fixed to the substrate. If the adhesion motif is not fixed covalently, there is an inverse effect on the cells (no survival, decrease in contractility). The adhesion motif serves as a bridge between the substrate and the contractile apparatus of cells and it must necessarily be fixed.

Adhesion peptide molecules, more particularly RGD peptide molecules, may advantageously be bonded to the (polymeric) structure of the (porous) solid substrate by a covalent bond, optionally via a spacer arm, more particularly a spacer arm of 30 to 40 Angstrom.

The (porous) solid substrate may be completely, partially or not biodegradable.

Advantageously, the solid substrate (and the biomaterial containing same) does not comprise tumour extracts (such as MATRIGEL®), more particularly Engelbroth-Holm-Swarm (EHS) tumour protein extract.

Advantageously, the method according to the invention is characterised in that said contractility substrate is a three-dimensional scaffold of crosslinked polymer, more particularly of crosslinked collagen, which has a porosity of 20 to 200 μm, and which optionally comprises adhesion peptide molecules, more particularly RGD peptide molecules, bonded covalently to the polymeric structure of the solid substrate.

The substrate may be associated with an agent, particularly a coupling agent.

The agent may be associated in free, absorbed, adsorbed or fixed form. The fixing may be reversible or association. The agent may be secreted by the cells, or the product of these cells including genetically modified cells, or produced by cells subjected to different stress (hypoxic, chemical, physical or other) or environmental conditions. The agent may be present in the substrate in vitro, in vivo before, during or after the implantation of the substrate. The agent may be optionally coupled to the substrate. The fixing may be reversible. The agent may be released by the substrate. The degradation of the substrate may enable the control of the release of the agent. The agent may be present in secretome or exosome form. The agents may be non-restrictively proteins, oligoproteins, optionally natural peptides, DNA, microRNA, mRNA, mitochondria. They may be growth factors, cytokines, chemokines, hormones, medicinal products for example, They may also consist of microvesicles or exosome type structures. These exosomes may be obtained optionally from several types of cells placed under conditions aimed at obtaining particular properties of these exosomes. The exosomes produced by a cell type may for example serve to "prime" another cell type to be transplanted thereon. For example, exosomes derived from cardiospheres may serve to activate by priming the fibroblast to be transplanted thereon in vivo and not the cell from which the exosomes originate.

The coupling agents may have a functional impact on the cells of the substrate or the substrate itself or a functional impact on the myocardial cells or the cardiac extracellular matrix, cellular recruitment and cell function particularly in the context of infarction (acute, subacute chronic), ischaemic cardiopathy, coronary ischaemia, non-ischaemic cardiopathy, myocarditis, heart failure, cardiogenic shock, myocardial conditions.

The substrate may be for example associated with agents promoting angiogenesis, anti-arrhythmic, contractility, controlling ventricular remodelling, infarction size, effect on cell adhesion, survival, proliferation, regeneration, signalling, apoptosis, migration, homing, differentiation, connection between the cells and cells with one another, contractility, cell recruitment, inflammatory and immune reaction control. The agent may be an immunosuppressant or regenerative agent. The immunosuppressant agents may promote regeneration in vivo. The agent may promote cardiac repair in several phases, by facilitating for example the use of subsequent or sequential or repetitive cell therapy, or several types of cells may be used. The agent may for example preserve the tissue for subsequent cell therapy. The various agents and effects may be associated.

It may consist of an agent promoting selectin-mediated cellular adherence with for example modification of the contractility substrate by modification with sugars. The agent may be optionally delivered in the substrate or in the target therapeutic zone of the functionalised via an additional device such as for example a ventricular restraint net, a device aimed at protecting or maintaining restraint support. The factor may be delivered at the same time or secondarily by the endovascular route endocoronary injection, endovenously, systemically, intramyocardial injection (endoventricle, epicardial), injection in the pericardium or release in the pericardium by devices not directly in contact with the heart but intended for the treatment thereof. The agent may also be produced by preparations situated in non-cardiac ectopic regions then optionally transferred in the region of the heart such as vascularised or non-vascularised flaps, or merely a region of interest transferred to the heart in free form. The use of epiploic flaps for example or substrates prepared in the peritoneal cavity and subsequently applied to the heart or pericardial cavity is within the field.

The agents in general including the cells according to the invention may be modified genetically using viral or non-viral genetic modification methods.

These agents include factors involved in the differentiation of the stem cells to contractile cells, the transformation of fibroblasts to myofibroblasts, factors involved in inducing MSC paracrine activity, suitable for modifying same or prolonging the secretion thereof or agents suitable for controlling cellular colonisation of the substrates including the inflammatory reaction.

The agents that may be associated with the substrate include interferon gamma, TGF beta 1, factors released the MSC for example, factors which will increase the Wnt signalling pathway, particularly the Wnt/beta-catenin cationic form of which Wnt3a.

The biomaterial may be subjected to a physical stimulus. The substrate may be physically stimulated by being subjected to a mechanical stimulus such as for example, electrical, mechanical elongation, compression extension, hooked to a spring or fixed (isometric stress), electromagnetic, thermal. The substrate may be electrostimulated. Electrostimulation plays a role in the differentiation to cardiomyocyte type contractile cells. Electrostimulation also plays a role in the differentiation of fibroblasts to myofibroblasts. Mechanical stimulation reduces the differentiation of MSC to adipocytic cells by inhibiting the SMAD pathways.

Advantageously, the method according to the invention is characterised in that said contractility substrate is
a solid, a gel or a hydrogel,
optionally crosslinked and/or optionally porous,
suitable for having the structure of a sponge or a foam;
and in that said substrate may be associated with an agent and/or may be stimulated physically.

The substrate may be developed in a bioreactor.

The cellularised substrate may be placed in a bioreactor. These bioreactors may with a mechanical stimulus, which may be produced by the liquid flow for example, physically stimulate said cellularised substrate. The application thus relates to a (novel) method for producing biomaterials in bioreactors associating various cell types and various stimuli. The electrical and mechanical stimuli may increase the differentiation to contractile cells and the paracrine activity of the associated cells.

The contractile biomaterial is specially adapted for regeneration therapy of myocardial tissue, particularly human myocardial tissue. It is particularly intended for subjects whose myocardial tissue is ischaemic and inflammatory, for example a myocardial tissue that has suffered from acute or chronic infarction.

The contractile biomaterial may particularly be intended to be administered by the pericardial route (in the case of coronary bypass procedures, or in the case of set-up of mechanical cardiac assistance), by sternotomy, by the mini-thoracotomy route, by the xiphoid route, or by pericardiotomy and/or by the mini-invasive route.

The (porous) solid substrate (and therefore the contractile material) may be of any shape and size deemed suitable by a person skilled in the art, particularly with respect to the intended medical application (for example with regard to the size of the target myocardial area), and with regard to the envisaged administration route.

It may for example be of round, oval, ovoid shape, and/or have a surface area of 0.5 to 10 $cm^2$, and/or with a thickness of 0.1 mm to 1 cm.

The biomaterial according to the application is contractile.

Advantageously, the contractile biomaterial according to the application has a compliance of 0.1 to 30 $kPa^{-1}$, more particularly of 0.1 to 3 $kPa^{-1}$ for myofibroblasts and more particularly of 5 to 15 $kPa^{-1}$ for other contractile cells.

The contraction and relaxation properties of the biomaterial according to the application are suitable for application on a myocardial tissue in vivo. These contraction and relaxation properties may be observed by applying a contraction stimulus inducing the reduction of a dimension of the biomaterial, and by stopping the application of this stimulus. The contraction stimulus may for example be by tetanic electrical stimulation (for example applied with alternating current) or by KCl chemical stimulation.

Advantageously, the relaxation of the cellular biomaterial may be of the same amplitude as the preceding contraction.

Advantageously, the cellular biomaterial fulfils a Hill curve, i.e. it has a contraction velocity which is in hyperbolic relation with the voltage applied thereto.

Advantageously, the contraction and relaxation kinetics of the cellular biomaterial are similar to or substantially not different to those of human placenta.

The cellular biomaterial according to the application may further have elastic elongation properties: it may for example be subjected to mechanical elongation of the order of 10% to 20%.

Remarkably, the contractile cellular biomaterial may be stored without being frozen: mere hypothermia is sufficient.

Indeed, the cellular biomaterial retains contractility properties after storing in isotonic solution for 5 days (particularly for 5 to 10 days) at a temperature greater than 0° C. and less than 10° C. (particularly a temperature greater than 0° C. and less than 4° C.).

The contractile cellular biomaterial may even retain an inducible paracrine activity after storing in isotonic solution for 5 days (particularly for 5 to 10 days) at a temperature greater than 0° C. and less than 10° C. (particularly a temperature greater than 0° C. and less than 4° C.).

The contractile cellular biomaterial may therefore be stored merely in a refrigerator. The cellular biomaterial may for example be stored in an isotonic solution, serum or plasma, or a (cell) culture medium. It may for example be contained in a cell culture plate, such as a 96-well plate, or in a cell culture tube (such as a 50 mL cylindrical tube).

Furthermore, the cellular biomaterial is immediately usable following the storage under hypothermic conditions.

The application relates more particularly to the contractile cellular biomaterial as described hereinafter and illustrated above and to the medical applications thereof.

A contractile cellular biomaterial suitable for being obtained with the method according to the invention is suitable for myocardial tissue regeneration therapy and is characterised in that it comprises:
- an optionally porous solid substrate which has a compliance of 1 to 30 kPA$^{-1}$ (compliance with or without cell, more particularly without cell), and
- a contractile cellular tissue which is contained in the optionally porous solid substrate,
- the contractile cells comprising cells chosen from myofibroblasts, fibroblasts, myocytes, cardiomyocytes and muscle cells and progenitors of these cells.

It may further have an IFN gamma-inducible paracrine activity, the inducible paracrine activity comprising a T-cell immunosuppression activity.

The biomaterial may further comprise an adhesive, such as a fibrin adhesive, at the periphery thereof, this adhesive being intended to promote fixing of the biomaterial on the myocardial tissue. This adhesive is nonetheless optional insofar as the material may have spontaneous adhesiveness on the myocardial tissue.

Advantageously, the biomaterial may be stored at a temperature greater than or equal to 0° C., more particularly at a temperature greater than 0° C., more particularly at a temperature greater than 0° C. and less than 32° C., more particularly at a temperature greater than 0° C. and less than 10° C., particularly at a temperature greater than 0° C. and less than 4° C.

Advantageously, the biomaterial may be stored for more than 24 hours, for example for 5 days or more than 5 days (particularly up to 10 days).

The biomaterial may be stored in any type of container deemed suitable by a person skilled in the art, for example in the well of a 96- or 24-well plate, or a cell culture tube (for example a 50 mL cell culture tube).

The biomaterial may be stored in a medium such as a cell culture medium. Advantageously, the medium wherein (or the solution wherein) the biomaterial is stored or placed before administration does not have to be a hypothermic medium (or solution).

The biomaterial may be suitable for controlling cell migration in vitro and in vivo.

The biomaterial may enable targeted cell therapy by preserving the cells in the substrate in vivo and by preserving the pro-regenerative immunosuppressant phenotype thereof.

The biomaterial according to the application is particularly intended to be used in the treatment of acute (0-7 days), subacute (7 days to 1 month) or chronic (after 1 month) infarction in order to limit the size of the infarction, preserve the myocardial tissue, control ventricular remodelling, promote angiogenesis, promote cardiac regeneration. It may be used for the treatment of myocardial insufficiency, particularly of ischaemic or post-infarction myocardial insufficiency (by healing the infarcted myocardial tissue and/or restoring contractility of the infarcted myocardial tissue). The biomaterial with the secretion of very numerous immunosuppressant and anti-inflammatory agents may also be of interest in myocarditis. It may also be of interest in inflammatory cardiac conditions such as for example rheumatic diseases.

The biomaterial according to the application is particularly intended to be used in the treatment of dilated or hypertrophic cardiomyopathy, myocarditis, pathological (or normal) heart ageing, myocardial fibrosis, heart transplant rejection, infectious heart disease (for example Chagas disease).

The biomaterial according to the application may be used in the regenerative (or healing) treatment of cardiac tissue, muscle tissue or non-contractile human tissue, more particularly in the treatment of post-infarction myocardial insufficiency. It may particularly restore myocardial tissue contractility.

The biomaterial may also be implanted in contact or in contractile, not necessarily cardiac, muscle tissue, such as muscle tissue for delivering agents intended to treat muscles or subjects in general.

The biomaterial may also be suitable for delivering in vivo a targeted therapy after application in contact with pathological tissue to promote the regeneration thereof. The substrate makes it possible to preserve the cells at a distance from the inflammatory reaction and preserve the pro-regenerative immunosuppressant phenotype in vivo. The engagement of the cells in contractile structures will prevent the migration thereof in vivo. Therefore, there will be cells retained in the delivery site thus the possibility of delivering a targeted therapy. Possible application for example on the liver.

The approach that we have for the storage, transfer and delivery of multipotent MSC is an approach that does not require freezing of the cells at least during the final phase. The approach therefore consists of not using multipotent MSC but of differentiating same in a 3D substrate with suitable factors. This substrate will enable them to interact with one another and with the substrate such that these cells will be suitable for being organised in tissular structure such as bone, cartilaginous, adipose tissue for example, In these structures, the MSC may be transferred under hypothermic conditions >0°, preferably between 0-10° C.

The following examples are given merely by way of illustration. They in no way limit the invention.

EXAMPLES

Example 1: Production of a Contractile Biomaterial

Preparation of the Porous Solid Substrate

Four types of matrixes were produced:
a dehydrothermal (DHT) crosslinked collagen matrix,
a DHT-crosslinked collagen matrix comprising adhesion peptide molecules, namely RGD (Arg-Gly-Asp) molecules,
a genipin-crosslinked collagen matrix,
a genipin-crosslinked collagen matrix comprising RGD peptide molecules.

The DHT-crosslinked matrix was produced. The matrix obtained by DHT corresponds to the Bard ULTRAFOAM™ matrixes. The matrix was manufactured with type I and type III collagen and used as a haemostatic sponge. The initial collagen is soluble in a 0.5% w/w collagen solution in 0.05 M pH 3.5 acetic acid. The preparation is dried by controlled cooling to obtain sponges. The pore size and the distribution are essentially dependent on the rate of freezing (0.25-1° C./min), the final freezing temperature of (−90° C. to −5° C.). This sponge is then subjected to DHT crosslinking (105° C. for 16 hours for a pressure less than 100 mTorr) to introduce covalent bonds between the collagen chains without denaturing same of gelatin. The collagen fibres spontaneously tend to group together in a porous structure. This capability remains present with gelatin but the porosity is lower. During freezing, a thermal gradient may be performed to orient the substrate.

The matrix may also be produced in the form of porous gelatin foam ("foam templating").

A gas phase (nitrogen) is generated by reaction between sulphamic acid and sodium nitrite in a gelatin solution and in the presence of a surfactant polymer and SDS. The foam is prepared at 45° C. then placed at 5° C. for gelling. After purification, the physical gel is self-crosslinked with EDC and may be freeze-dried. The gaps and interconnections are of the order of 230 and 90 microns, respectively.

The genipin-crosslinked collagen matrix was produced. We observed that it was possible to crosslink the substrate with genipin (concentration<10 mM for 24 hours at 37° C., optimal concentration 1.5 mMol for 24 hours at 37° C.). Genipin was used for concentrations between 0.1 and 10 mM. For higher concentrations, genipin is toxic for the cells. Crosslinking may be carried out at room temperature or at 37° C. The crosslinking of the substrate is accompanied by more or less extensive crosslinking of the substrate. Crosslinking may be carried out for up to 3 days but tissues may be crosslinked for 1 month. The greater the increase in temperature, the more rapid the crosslinking.

For the covalent fixing of the RGD motif, we used a heterobifunctional crosslinker, sulfo-LC-SPDP, which makes it possible to couple an NH2 site of the peptide with an amine site present on the collagen. By modifying both the collagen and the peptide, we were able to fix the molecule unidirectionally with the introduction of a spacer arm of 36 Angstrom. Fixing time 48 hours. During fixing, thiol groups are released in the medium and allow us to ascertain both the number of NH2 sites available on the collagen and also the number of RGD molecules fixed to the substrate.

The optimal spacer is around 36 Angstrom (40-50 Angstrom). With a progressive effect of zero Angstrom to 35. Preferably, the crosslinker may be flexible and hydrophilic.

In an embodiment, the crosslinker may be made of amino acid only without participation of the agent used for crosslinking in the spacer. Glycine type amino acids may be used. The spacer for each glycine is about 3.4 Angstrom. It is possible to then have oligopeptides which contain the motif GRGDS (SEQ ID NO: 1), and the spacer -GSGGGGGGS (SEQ ID NO: 2) or -GGGGGGGGG-GRGDS (SEQ ID NO: 3). The presence of an S amino acid improves the presentation of the peptide on the membrane. The oligopeptide containing RGD will then be fixed to the —NH2 of the collagen by a conventional Azide or isocyanate type chemical reaction. It is also possible to use - - - CGSGGGGGGGS-GRGDS (SEQ ID NO:42) or CGSGGGGGGGS-GRGDS (SEQ ID NO:42) and use Succinimidyl iodoacetate C6H6INO4 (SIA) (zero crosslinked for coupling the peptide to the collagen). The idea is having a spacer of 36 Angstrom essentially made of glycine. It is possible to have a spacer arm wherein a portion is a synthetic polymer such as made of HOOC—H2CH2C-PEH8-NH2 and use SIA to fix the oligopeptide C-GRGDS with an —SH group and EDC/NHS or EDC or Sulfo-NHC to bind the carboxylic group to the —NH2 group of the collagen. Using Sulfo-LC-SPDP, it is possible to limit the cost using a modified peptide containing an —SH group such as a cysteine of the type -C-GGGG-GRGDS (SEQ ID NO: 4). Therefore, this gives a cysteine with a thiol group whereon it is possible to perform fixing on the collagen using Sulfo-LC-SPDP. The final fixing will give a spacer arm of 36 Angstrom.

For the matrixes comprising peptide G-RGDS, the "RGD" peptide was used as a rate of 1 mg per 10 mg of collagen. The RGD peptide molecules were fixed covalently to the collagen molecules of the substrate by functionalisation in solid heterogeneous phase, using sulfosuccinimidyl 6-(3'-(2-pyridyldithio)propionamido)hexanoate (sulfo-LC-SPDP).

Crosslinking with genipin did not modify the fixing of the adhesion molecules. However in vivo, matrix reuptake control in immunocompetent rates is greater if the matrixes are crosslinked prior to modification with the adhesion molecules.

In each matrix produced, the pore size was between 20 and 200 μm.

Each matrix produced was cut in the shape of disks 6 mm in diameter and 3 mm in thickness. When submerged in the culture medium, the thickness of the matrixes decreases by 20%. Cutting of the matrix is unimportant as the cells have the ability to migrate into the matrix. Optionally to improve the initial seeding if the cell concentrations are very high, a short centrifugation may be used. The thickness of the human myocardium is 10 mm.

Each disk may individually serve as a porous solid substrate.

Isolation of Mesenchymal Stem Cells.

Mesenchymal stem cells (MSC) were isolated from haematopoietic bone marrow present human femoral heads. These femoral heads were obtained from tissues sacrificed during orthopaedic prosthetic hip replacement. The cells were isolated on the mononuclear fraction of the cells of this bone marrow. The iliac crest was aspirated from the resected femoral head. Each aspirate (3-30 mL) was collected in an EDTA tube. The aspirates were diluted 1:1 in a Hank's Balanced Slat Solution (HBSS). The mononuclear cells were collected by centrifugation with a density gradient of 1000 G for 20 min through tubes containing UNI-SEP Maxi (polysucrose-sodium metrizoate). The mononuclear fraction is collected and washed on an HBSS solution. The cells were stained with Trypan blue to identify and collect the live cells.

The cells collected were cultured on an expansion medium in standard cell culture vials (NUNC® 75 cm$^2$) at a rate of 250,000-300,000 cells per vial. The cultures were incubated at 37° C. in 5% $CO_2$.

The expansion medium was a DMEM (low glucose content Dulbecco's Modified Eagle Medium, SIGMA-ALDRICH®) medium supplemented with 0.05 mg/mL of gentamycin, 2 IU/mL of heparin, 0.001% of 2-Mercaptoethanol (SIGMA-ALDRICH®), 1% non-essential amino acid, and 10% platelet lysate.

The platelet lysate was prepared using platelet-rich plasma (PRP) obtained from the French blood bank (Etablissment Frangais du Sang) and tested negative for HIV, HTLV, HCV and HBV viruses. The bags containing PRP plasma are stored at −80° C. and heated to 37° C. in a water-bath. After heating, PRP plasma from multiple donors is mixed and centrifuged at 14,000 G for 10 min to remove platelet particles and membranes. The platelet lysate supernatant was collected and frozen at −80° C. until use. The platelet lysate was tested for the absence of bacterial endotoxins, haemoglobin (purity), pH, total proteins, albumin, osmolarity, sterility and the absence of *Mycoplasma*.

The cells adhering to the culture dish plastic (after 24 hours of contact with the plastic surface), and exhibiting the panel of markers of MSC (cells positive for CD105, CD73 and CD90, and negative for CD45, CD34, CD14, CD19 and HLA-DR) were selected. These cells are capable of being differentiated to adipocytes, chondroblasts and osteocytes.

The isolated MSC may be placed in culture on expansion medium until use (the medium being replaced when the cells reach confluence, the cells being detached with trypsin for 5 min at 37° C.

During the preparation process, the MSC may be optionally frozen. The MSC may be frozen until at least the 10$^{th}$ passage. After thawing, the MSC may be once again amplified in conventional amplification media before being associated with the substrate. The biomaterials obtained will then no longer be frozen for storage, delivery and transfer.

Induction of the Differentiation of the Mesenchymal Stem Cells to Cells Forming a Contractile Tissue Contained in the Porous Solid Substrate.

The porous solid substrates were placed in culture well plates at a rate of one substrate per well. The isolated MSC were added at a rate of 10$^5$ cells per substrate in a volume of 10 µl of expansion medium (containing platelet lysate, and therefore TGF beta 1). They may be deposited on the surface of the porous solid substrate. The plates are incubated at 37° C. for 9 to 30 days. The expansion medium was replaced every two days. The contractile and immunosuppressant properties of the cells are preserved during this period. After 1 month, the metalloproteinase enzymes secreted by the MSC will progressively result in destruction of the substrate and less contractility if the preparations are kept at 37° C.

The MSC migrate in the volume of the porous solid substrate and colonise same homogeneously.

After four days, the MSC are massively (more than 80%) differentiated to cells forming a contractile tissue inside the pores of the porous solid substrate from the 8$^{th}$ day.

If desired, the incubation may be continued for up to at least 45 days.

The collagen substrate that we used may be digested with type II collagenases (for 15 min-1 hour at 37° C.). The cells may then be retrieved and it is possible to analyse the number thereof, survival thereof, and we developed a specific cytometry for alphaSMA so as to quantify these cells in the preparation. It is also possible to perform co-labelling for the alphaSMA cells and the other mesenchymal markers. However, in our preparations in keeping with our semi-quantitative histological analysis, the majority of the cells are alphaSMA cells and express the mesenchymal cell markers.

In the substrates, the viability of the cells is of the order of 95% outside stress conditions. We did not place a difference in survival in the presence or absence of RGD. There is only little cell proliferation merely 20-30% over 2 weeks. However, massive cell differentiation is observed. Between the matrixes with or without RGD, the differentiation level is the same; however, the association of alphaSMA with the contractile apparatus may be different and could explain the difference in contractility of the different preparations.

We also analysed these cells in conventional microscopy. We did not observe a difference between outside and inside the substrate. Interestingly, initially, the cells are capable of colonising any type of substrate. They may be placed at the end of a cylindrical substrate and they will colonise the substrate probably due to the size of the pores thereof. The colonisation tends to take place from the inside outwards. If applied to young cell preparations, the cells will pass from one substrate to another by forming bridges. Secondarily, a relatively large layer is formed on the surface. However, if substrates are applied in contact with these cells, they no longer migrate. We confirmed in confocal microscopy the colocation for the alphaSMA and myosin markers.

The contractile tissue comprises cells which express the myofibroblast marker alphaSMA. Therefore, it consists of contractile cells.

In electron microscopy, even in the absence of RGD peptide molecules, cells were observed with a stress band organisation and a sarcomeric type organisation, with an alternation of bands about every micrometre: cf. FIG. 1.

Under the electron microscope, the cells differentiated from MSC exhibited the characteristics of myofibroblasts with the presence of basal membrane, a very developed endoplasmic reticulum, a particulate cell organisation with the fibronexus type extracellular matrix with and adherent junction type intercellular junctions. In FIG. 1, the rectangles outlined delimit the identifiable zones of contractile filament proteins. The arrows show a regular interruption of these filaments by dense bodies or possibly a sarcomere. Regardless of the organisation of the apparatus, a terminal organisation of the contractile apparatus is observed herein in the contractility substrate according to the application.

Interestingly, the mesenchymal cells also expressed stress bands with an alternation of bands of 1 micrometre suggesting a sarcomeric type organisation. These structures are abundant and not only in the membrane adherence zone. We saw these structures in collagen substrates with and without adhesion molecule such as RGD, and also in chemical crosslinked substrates.

This demonstrates in vitro the formal link between mesenchymal stem cells and myofibroblast type contractile cells. We demonstrate that in vitro MSC may be differentiated to cells other than chondrocytes, osteocytes and adipocytes, namely to fully differentiated myofibroblasts. The interactions between the cells and the extracellular matrix, and among cells, are extremely developed.

These organised structures of the in vitro contractile apparatus have not, to our knowledge, been demonstrated on contractile cells derived from MSC in 2D cultures. More particularly, these stress bands and the terminal organisation of the contractile apparatus have, to our knowledge, never been detected with MSC-derived cultures. The biomaterial according to the application therefore enables the terminal differentiation of the contractile cells.

Tests conducted in the absence of platelet lysate show an absence of differentiation of MSC to contractile tissue. Adding TGF beta 1 restores the differentiation of the MSC to contractile tissue in the porous solid substrate.

It is also possible to use MSC present in cell cluster preparations such as "cardiosphere" preparations. Cardiospheres are the cells currently under development for post-infarction regeneration. Allogenic or autologous cardiospheres may be used. Human cell clusters (cf. "cardiospheres") are obtained from human myocardial biopsies and are enriched with MSC type stem cells and C-kit+ cells.

Figure 5A:
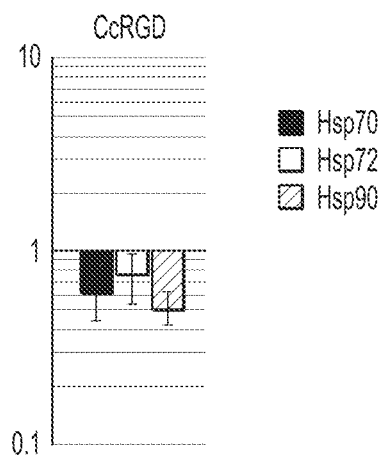
FIGS. 5A-5D show the migration of the cells from the cardiospheres in the substrates (change vs. HCSps (log scale)), the cells do not remain in cluster form (FIG. 5B) but migrate and are distributed throughout the substrate (FIG. 5C). Cardiac marker induction (FIG. 5D) and a decrease in the stress proteins Hsp70, Hsp72, Hsp90 (FIG. 5A) was observed. Akt activation in the MSC cells was also observed.
Figure 5B:
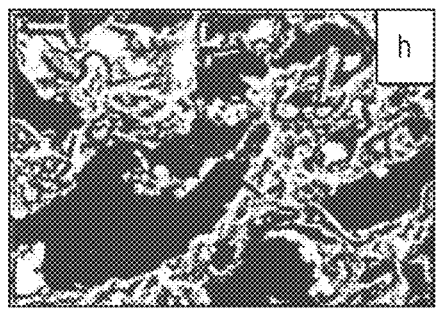
Figure 5C:
Figure 5D:
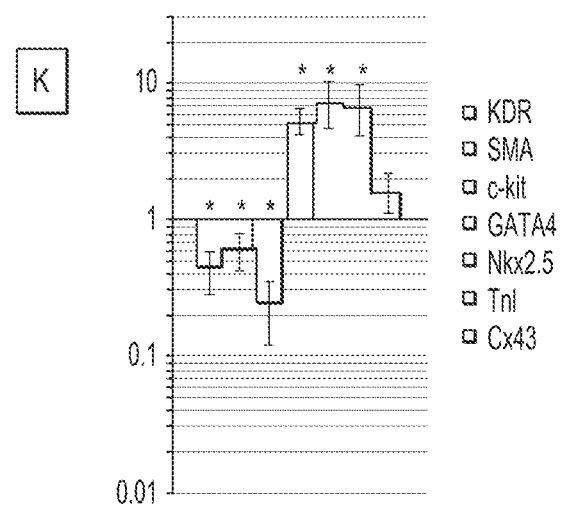

The cardiospheres were placed in vitro in DHT RGD collagen matrixes or gelatin foams crosslinked with EDC/NHS for 7 days. In the 3D RGD collagen substrate the cells, the cells migrate outside the cluster (FIG. 5B) and colonise the entire substrate (FIG. 5C). There is a significant increase in the cardiac markers (FIG. 5D). There is also a decrease in the Stress proteins Hsp70, Hsp72 and Hsp90 (FIG. 5A). In other cell preparations, we also observed activation of the Akt survival pathway in the cells according with the substrate. Akt activation could in part explain the superior survival of the cells under hypothermic stress conditions.

Example 2: Contractility of the Biomaterial

The contractility of the biomaterials of example 1 above was tested by electrical stimulation (tetanic contraction induced in alternating current) and by chemical stimulation with KCl (0.05 M), according to the same protocol as that applied to placental tissue as described in Lecarpentier et al. 2013 (Placenta 34: 1163-1169) and Lecarpentier et al. 2015 (PLoS ONE 10(11); e0142471).

The biomaterials of example 1 were stored in a refrigerator at a temperature greater than 0° C. and less than or equal to 4° C. until use. They were then placed in a bath at 30° C. for 30 min, and subjected to the contractility tests.

For the mechanical stimulations, the tests may be performed after merely heating at ambient temperature. The preparations are extremely stable throughout the measurements which are carried out over several hours with the same responses at experiment start and end. The preparation may be placed in a refrigerator and the same type of response observed on subsequent days.

Figure 2:
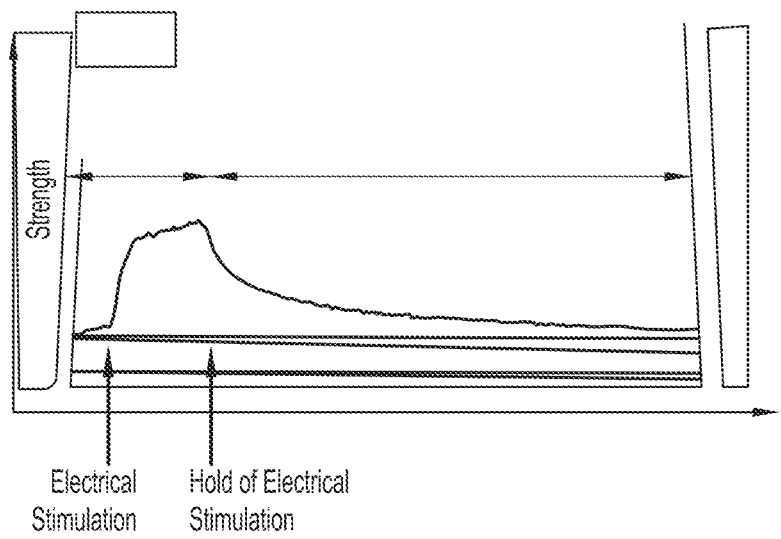
FIG. 2 illustrates the contractility result exhibited by a biomaterial according to the application (collagen matrix crosslinked by DHT; MSC differentiated to myofibroblasts to at least 80%). The contraction and relaxation kinetics are similar to those of placental tissue (cf. example 2 hereinafter).

After tetanic electrical stimulation, there is significant shortening of the substrates. This shortening ceases when the stimulation ceases (cf. FIG. 2). Interestingly, the contraction and relaxation kinetics are very similar with a return to the basal state with the same kinetics. Like contraction, relaxation is a phenomenon triggered by the cellular contingent associated with the substrate. Relaxation is a dynamic and non-passive mechanism (if the relaxation was passive, there would be difficulty filling the heart, which could result in diastolic heart failure due to ventricular filling difficulty). Remarkably, the contraction and relaxation kinetics are similar to those of placental tissue.

The tests were then reproduced by maintaining the contraction stimulus (electrical current or KCl) and by adding to the medium an actin-myosin interaction inhibitor (namely 2,3-butanedione monoxime (BDM) at 4 mM), or a nitric oxide and cyclic guanosine monophosphate (NO-cGMP) pathway activator (namely isosorbide dinitrate (ISD or RISORDAN™) at $1.7 \cdot 10^{-4}$ M). The induction of NO in the preparations means that the preparations are viable and extremely functional since at least 4 intracellular cascades are involved to obtain relaxation.

Figure 3A:
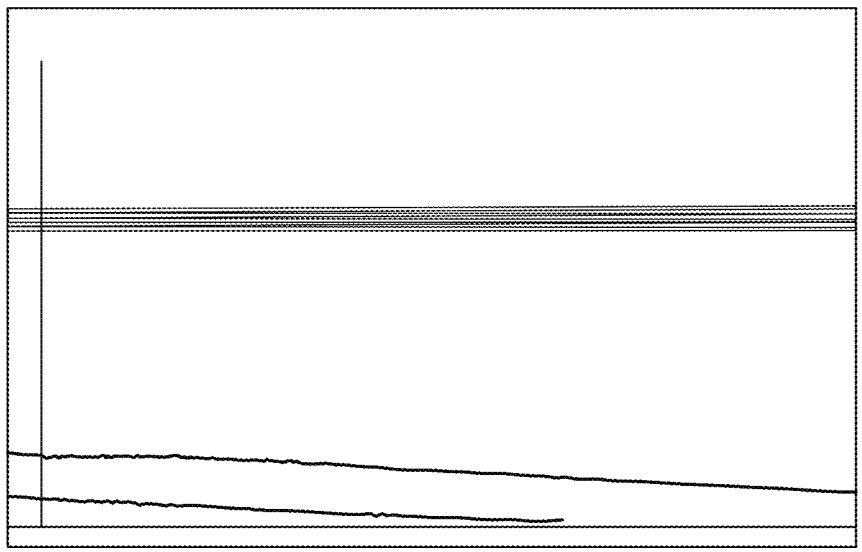
FIGS. 3A and 3B illustrate that the relaxation property of a biomaterial according to the invention is indeed an active phenomenon, and not a passive phenomenon (relaxation with elongation [top curves in FIGS. 3A and 3B] and with reduction of the developed force [bottom curves in FIGS. 3A and 3B]).
Figure 3B:
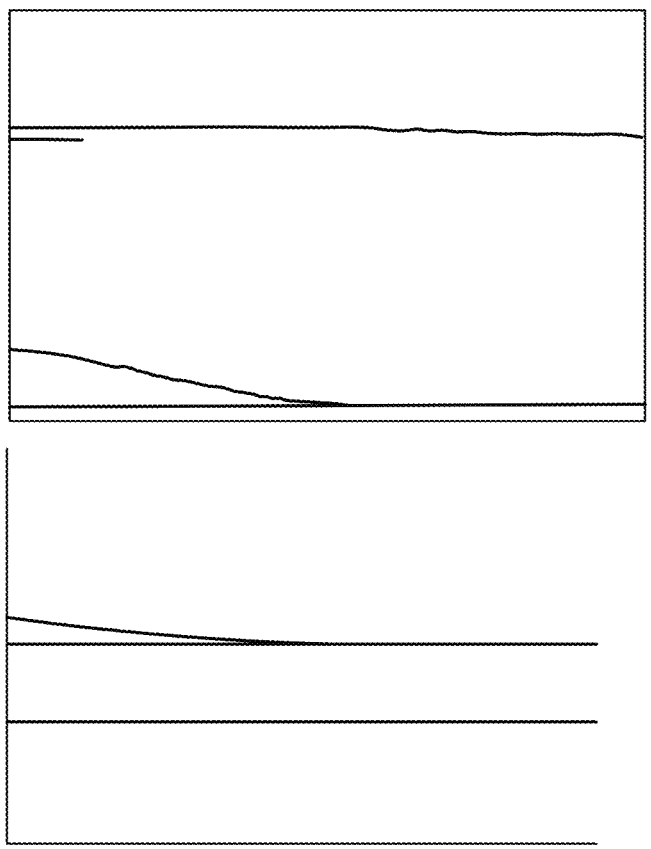

The results are illustrated by FIG. 3A (cases of a biomaterial with DHT-crosslinked collagen matrix and with RGD peptide molecules, under tetanic electrical stimulation and with RISORDAN™ inhibition) and by FIG. 3B (case of a biomaterial with DHT-crosslinked collagen matrix, under 0.05 M KCl stimulation, and BDM inhibition). It was observed that the inhibitor (RISORDAN™ or BDM) induces a relaxation of the same if the stimulus having triggered contraction (electrical current or KCl) is maintained. This demonstrates that relaxation is an active phenomenon mediated by the contractile units (actin myosin) of the tissue of the biomaterial.

It was observed that the presence of adhesion molecules (RGD peptide) increases the contractility parameters, in general by a factor of 2 or 3.

Figure 4:
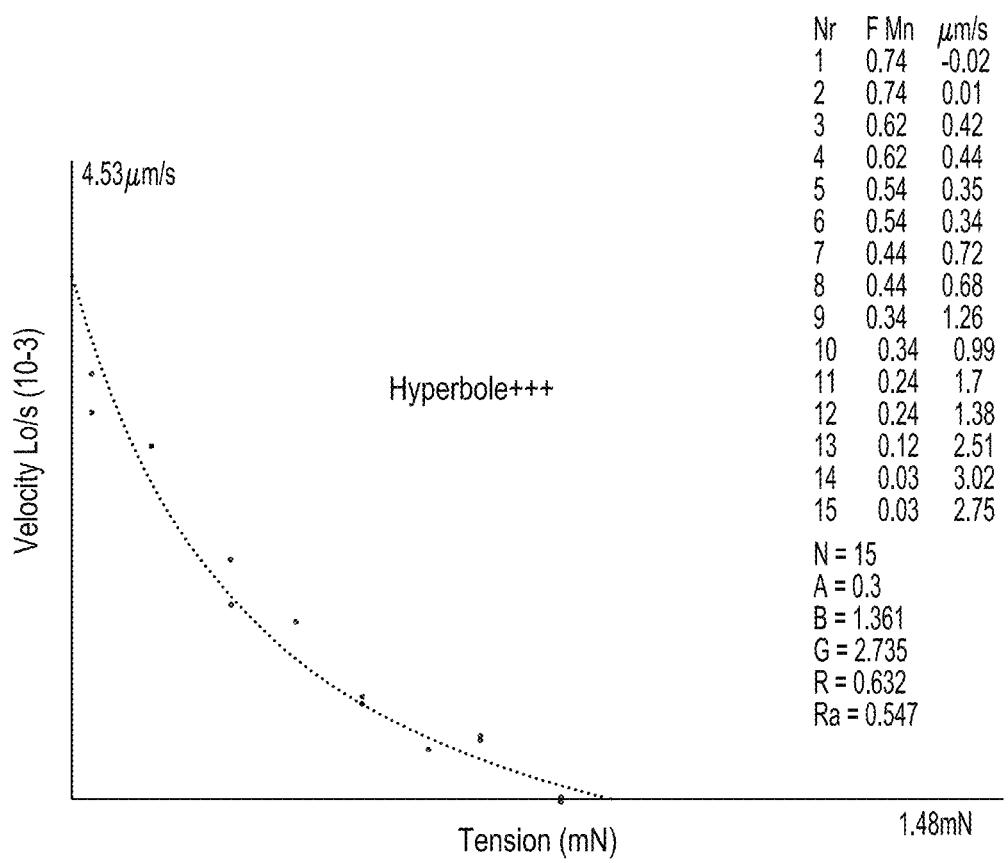
FIG. 4 shows that a Hill curve was established for a biomaterial according to the application (biomaterial with collagen matrix crosslinked using DHT, and stored at a temperature greater than 0° C.—in this instance about 4° C.). The Hill curve (hyperbole) is specific to contractile tissues (x-axis: tension (mN); y-axis velocity Lo/s($10^{-3}$); cf. example 2 hereinafter).

Completely exceptionally, a Hill curve was established (cf. FIG. 4), which is characteristic of the contractile muscle tissues after KCl stimulation or electrical stimulation. The curves that we observed are very superimposable on those which have further been described for explanted human placental tissue.

The compliances of the substrates were determined. For the collagen substrate, the compliance without cells was 0.4 kPa. The compliance of the substrates colonies by the cells was 1.5. kPa.

Example 3: Induction of a Paracrine Activity

T lymphocytes were labelled with the cytoplasmic intracellular fluorescence marker CFSE (the fluorescence whereof is divided by two at each cell division), and were activated by antiCD3 and antiCD8 for 48 hours.

The biomaterials of example 1 were incubated with 500 IU/ml IFN gamma for 7 days.

Before and after this incubation with IFN gamma, the supernatants of the biomaterials were placed in contact with the activated and labelled T lymphocytes.

Tryptophan consumption was measured in the incubation medium (according to the Boxam and Warren method), The tryptophan consumption in the medium in the MSC is due to IDO activation. In the incubation medium of the biomaterials non-stimulated with IFN gamma, there was practically no tryptophan consumption. On the other hand, in the incubation medium of the biomaterials stimulated with IFN gamma, high tryptophan consumption was observed. It is of the same order of magnitude as that which would be observed with a standard 2D culture of non-differentiated MSC cells. However, there is very little cell proliferation in the biomaterial with respect to a (standard 2D) culture of non-differentiated MSC. The paracrine function of the biomaterial is therefore superior to that of a (standard 2D) culture of non-differentiated MSC.

The CFSE fluorescence was measured. It can be observed that the biomaterial (with MSC differentiated to myofibroblasts at more than 80%) inhibits the proliferation of the B lymphocytes whether they are based on crosslinked collagen or collagen crosslinked by DHT with RGD peptide molecules.

The expression of different factors associated with a paracrine function, and particularly the expression of cytokines and metalloproteinases, was measured.

An increase in the expression of the metalloproteinases MMP9. MMP2 and MMP14, after IFN gamma stimulation of the biomaterial, and particularly an increase in the secretion of MMP9 and MMP2, more particularly MMP9, was particularly observed (in particular on D7).

It was therefore observed that, even though, in the biomaterial, the MSC were differentiated to cells forming a contractile tissue, the inducible paracrine activity was not lost. It even appears to have increased.

Example 4: Non-Frozen Storage

The biomaterials of example 1 were stored for 10 days in a refrigerator (at a temperature of about 4° C.). The contractility and the paracrine function of these biomaterials were measured as described in examples 2 and 3 above. No impairment of contractility or of paracrine function was detected. The biomaterials may therefore be stored non-frozen, and are immediately functional.

In contrast, (non-differentiated) MSC stored by freezing only recover a paracrine activity after 7 days after thawing.

It was also possible to send the biomaterials by post conventionally in polystyrene containers. The biomaterials being in the culture medium thereof containing serum and antibiotics in 50 mL tubes. Inside the polystyrene to keep the low temperature around zero degrees with "ice pack" cooler cold packs and optionally dry ice avoiding direct contacts with the tube containing the biomaterial. On arrival, the tubes containing the biomaterials are stored in a refrigerator between 0-4° C. In some cases, preparations arrived after 6 days with no particular problem even if the dry ice was no longer present.

Ice packs suitable for preventing freezing such as materials used to deliver pharmaceutical products of the CRYOPAC type suitable for maintaining defined temperatures preferably herein between +2° C. and +8° C. may be used. The temperature in the container may optionally be monitored. If it is desired to change the preparation medium, the biomaterials with the cells may be placed in another container with the suitable medium. Optionally, the change may be carried out in an operating theatre or under a suitable laminar flow hood.

A further solution, so as not to expose the preparation to air, is that of making this change in a confined environment.

One solution may be to have a plurality of vessels in series with in the first vessel the desired final medium, in the middle vessel the cells with substrate and the $3^{rd}$ vessel optionally being empty and serving as a waste bin. The number of vessels and the organisation thereof may be varied. They do not all necessarily have the same volume. There may be a presence of communication via channels between the vessels with the possibility of having closure or non-return systems. There may also be bacterial filter systems therein.

Example 5: Post-Myocardial Infarction Therapy on Animal Model

The biomaterials of example 1 were administered to rats serving as myocardial infarction models.

A myocardial infarction model was developed in rats as described in Vallée et al. 2012 (Stem Cells Translational Medicine 1: 248-260). OFA (Oncins France strain A) rats, of 250 g each, were obtained from the company CHARLES RIVER (Wilmington MA; USA). The rats were immunodepressed with tacrolimus (8 g/kg/day in two injections) before the operation and for 45 days. The rats were anaesthetised with a mixture of ketamine 100 mg/kg and xylazine 10 mg/kg administered by intraperitoneal injection, and were ventilated after tracheal intubation. A left thoracotomy were performed to approach the heart and the pericardial cavity. Myocardial infarction was produced by definitive ligation of the anterior intraventricular artery with PROLENE™ 6/0 suture. The infarction is accompanied by ST segment elevation on the electrocardiogram, localised cyanosis in the region downstream from the occluded vessel and akinesia of the area (in this instance of the anterior myocardium).

The size of the infarction and the functions of the left ventricle were measured by MRI on D2, D7 and D45. The ligation of the anterior intraventricular artery induces an infarction of 25% in size, which remains stable over time. The left ventricular ejection fraction (which is 68% at the normal outside ligation and infarction) changes to 53% on D2, then to 45% on D7 and D45.

The biomaterials of example 1 were stored for 7 days in a refrigerator (temperature of 4° C.), then were placed in contact with IFN gamma for 5 days at ambient temperature. The biomaterials were placed on the infarcted area (with optional suture with PROLENE™ suture).

The size of the infarction is merely 10% on D7 (biomaterial of example with DHT-crosslinked matrix and MSC differentiated to myofibroblasts), whereas it remains at 25% with an injection of non-differentiated MSC.

The left ventricular ejection fraction is 60% on D2, 59% on D7 and 58% on D45 biomaterial of example 1 with DHT-crosslinked matrix and MSC differentiated to myofibroblasts, whereas it is 54%, 52% and 49% on D2, D7 and D45, respectively, with a biomaterial wherein MSC differentiation is not induced (non-contractile biomaterial).

The biomaterial of example 1 (DHT-crosslinked collagen matrix; MSC differentiated to myofibroblasts) makes it possible to reduce post-infarction ventricular dilation particularly diastolic ventricular distension. It further makes it possible to increase the segmental systolic contractility, which the non-contractile biomaterial does not achieve (MSC differentiation not induced).

The human MSC cells transfected with RLuc were identified in vivo after injecting the substrate for luciferase on D1, D4, D8 and D25. With collagen patches with non-contractile multipotent cells, there is a massive decrease on D4 of the order of 75% whereas this decrease is delayed with contractile patches containing RGD or not. At 1 month with collagen-based contractile patches, 30% of the cells are still present and 50% if the contractile patches contain collagen-RGD.

Example 6: Possibility of Using this Approach Outside the Heart

In vivo, the collagen substrate improves the initial retention of the cells in contact with undifferentiated multipotent cells. The MSC cells have a secondary migration however in the collagen matrixes. The differentiation of the MSC to contractile cells makes it possible to delay this migration to more than 2 weeks. It was demonstrated that MSC do not necessarily have to be present permanently but the initial graft take rate thereof determines a large portion of the effect thereof.

We developed a system for tracing cells in vivo after transfecting these cells with the luciferase gene. The multipotent human MSC were labelled. The multipotent MSC cells were cultured for 48 hours in the substrates. After 4 days, merely 50% of the cells locally disappeared and less than 10% of the cells remained from the $8^{th}$ day up to 1 month. These results are however superior to those obtained if the MSC are injected in free form into the thigh where less than 10% of the cells are present after 24 hours. Therefore, the presence of the cells in a substrate improves the retention thereof on D1. We compared substrates with D9 differentiated cells to contractile structure. With these patches on D4, practically 100% of the cells are still present. From D8, there is a decrease in the number of cells and 50% of the cells on D11. At 1 month, 20% of the cells still remain. With a slight superiority of the collagen patches with RGD. The differentiation of MSC into contractile structures reduces the secondary migration of these cells in vivo.

The invention claimed is:

1. An artificial contractile cellular biomaterial, comprising contractile cells forming an artificial contractile tissue in a manufactured three-dimensional solid porous contractility substrate seeded with cells and having a compliance of 0.1 to 30 $kPa^{-1}$, wherein:
   the contractile cells of the artificial contractile tissue are bonded together by intercellular junctions;
   the artificial contractile cellular biomaterial has the property of contraction upon electrical stimulation, with onset of forces and shortening and with a contraction velocity which is in hyperbolic relation with a voltage applied upon the electrical stimulation, and has the property of relaxation with the same amplitude as the preceding contraction;
   the artificial contractile biomaterial has stress bands and a terminal organization of a contractile structure;
   the contractile cells consist of fibroblasts and myofibroblasts derived from multipotent mesenchymal stem cells (MSC) that retain MSC cell markers CD105, CD73 and CD90, which do not appear in differentiated cells, and are negative for CD45 and HLA-DR;
   the artificial contractile tissue has inducible or induced paracrine activity comprising T lymphocyte proliferation inhibition and/or indoleamine 2,3-dioxygenase (IDO) activation; and
   the artificial contractile cellular biomaterial is designed to have the properties of retaining contractility and retaining inducibility of, or induced, paracrine function or activity after storage in a range of 5 to 10 days in isotonic solution at a temperature greater than 0° C. but less than 10° C. by rendering the contractile cells resistant to said temperature and with the artificial contractile cellular biomaterial being immediately available and functional after storage for administration to a patient in need of repair or healing of contractile tissue comprising myocardial tissue and infarcted myocardial tissue.

2. The artificial contractile cellular biomaterial according to claim 1, which is in a form suitable for administration by pericardial route, by sternotomy, by mini-thoracotomy route, by xiphoid route, or by pericardiotomy and mini-invasive route.

3. The artificial contractile cellular biomaterial according to claim 1, wherein the artificial contractile cellular biomaterial retains contractility and retains inducibility of, or induced, paracrine function or activity after storage in a range of 5 to 10 days in isotonic solution at a temperature greater than 0° C. and less than 4° C.

4. The artificial contractile cellular biomaterial of claim 1, which secretes, or is capable of secreting upon induction of paracrine activity, at least one metalloproteinase selected from the group consisting of MMP9, MMP2 and MMP14.

5. The artificial contractile cellular biomaterial of claim 1, wherein the contractile cells express cellular differentiation marker alpha SMA.

6. The artificial contractile cellular biomaterial of claim 1, wherein the contractile cells are from MSC that colonized the solid porous contractility substrate uniformly.

7. The artificial contractile cellular biomaterial of claim 1, wherein the solid porous contractility substrate is chemically or physically crosslinked.

8. The artificial contractile cellular biomaterial of claim 1, wherein the solid porous contractility substrate is chemically crosslinked with genipin.

9. The artificial contractile cellular biomaterial of claim 1, wherein the solid porous contractility substrate has a compliance of 0.4 to 20 $kPa^{-1}$ with or without the contractile cells.

10. The artificial contractile cellular biomaterial of claim 1, wherein the solid porous contractility substrate has a compliance of 0.5 to 15 $kPa^{-1}$ with or without the contractile cells.

11. The artificial contractile cellular biomaterial of claim 1, wherein the solid porous contractility substrate has a compliance of 0.5 to 5 $kPa^{-1}$ with or without the contractile cells.

12. The artificial contractile cellular biomaterial of claim 1, wherein the solid porous contractility substrate is a three-dimensional scaffold of crosslinked polymer having a porosity of 20 to 200 μm, and which optionally comprises adhesion peptide molecules bonded covalently to the polymeric structure of the solid porous contractility substrate.

13. The artificial contractile cellular biomaterial of claim 12, wherein the adhesion peptide molecules bonded covalently to the polymeric structure of the solid porous contractility substrate are arginylglycylaspartic acid (RGD) peptide molecules.

14. The artificial contractile cellular biomaterial of claim 12, wherein the crosslinked polymer is crosslinked collagen.

15. The artificial contractile cellular biomaterial of claim 1, wherein the solid porous contractility substrate is manufactured from synthetic polymers.

\* \* \* \* \*

```
                       SEQUENCE LISTING

<160> NUMBER OF SEQ ID NOS: 42

<210> SEQ ID NO 1
<211> LENGTH: 5
<212> TYPE: PRT
<213> ORGANISM: Artificial Sequence
<220> FEATURE:
<223> OTHER INFORMATION: RGD peptide
<220> FEATURE:
<221> NAME/KEY: misc_feature
<223> OTHER INFORMATION: Synthetic

<400> SEQUENCE: 1

Gly Arg Gly Asp Ser
1               5

<210> SEQ ID NO 2
<211> LENGTH: 14
<212> TYPE: PRT
<213> ORGANISM: Artificial Sequence
<220> FEATURE:
<223> OTHER INFORMATION: RGD peptide
<220> FEATURE:
<221> NAME/KEY: misc_feature
<223> OTHER INFORMATION: Synthetic

<400> SEQUENCE: 2

Gly Ser Gly Gly Gly Gly Gly Ser Gly Arg Gly Asp Ser
1               5                   10

<210> SEQ ID NO 3
<211> LENGTH: 14
<212> TYPE: PRT
<213> ORGANISM: Artificial Sequence
<220> FEATURE:
<223> OTHER INFORMATION: RGD peptide
<220> FEATURE:
<221> NAME/KEY: misc_feature
<223> OTHER INFORMATION: Synthetic

<400> SEQUENCE: 3

Gly Gly Gly Gly Gly Gly Gly Gly Gly Gly Arg Gly Asp Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: RGD peptide
<220> FEATURE:
<221> NAME/KEY: misc_feature
<223> OTHER INFORMATION: Synthetic

<400> SEQUENCE: 4

Cys Gly Gly Gly Gly Gly Arg Gly Asp Ser
1               5                   10

<210> SEQ ID NO 5
<211> LENGTH: 6
<212> TYPE: PRT
<213> ORGANISM: Artificial Sequence
<220> FEATURE:
```

```
<223> OTHER INFORMATION: adhesion peptide
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: X is a hydroxyamino acid
<220> FEATURE:
<221> NAME/KEY: MISC_FEATURE
<222> LOCATION: (2)..(2)
<223> OTHER INFORMATION: X is a basic amino acid
<220> FEATURE:
<221> NAME/KEY: MISC_FEATURE
<222> LOCATION: (3)..(3)
<223> OTHER INFORMATION: X is a basic amino acid
<220> FEATURE:
<221> NAME/KEY: MISC_FEATURE
<222> LOCATION: (4)..(4)
<223> OTHER INFORMATION: X is a hydroxy amino acid
<220> FEATURE:
<221> NAME/KEY: MISC_FEATURE
<222> LOCATION: (5)..(5)
<223> OTHER INFORMATION: X is a basic amino acid
<220> FEATURE:
<221> NAME/KEY: MISC_FEATURE
<222> LOCATION: (6)..(6)
<223> OTHER INFORMATION: X is a hydroxyamino acid

<400> SEQUENCE: 5

Xaa Xaa Xaa Xaa Xaa Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: X is a hydroxy amino acid
<220> FEATURE:
<221> NAME/KEY: MISC_FEATURE
<222> LOCATION: (2)..(2)
<223> OTHER INFORMATION: X is a basic amino acid
<220> FEATURE:
<221> NAME/KEY: MISC_FEATURE
<222> LOCATION: (3)..(3)
<223> OTHER INFORMATION: X  is a basic amino acid
<220> FEATURE:
<221> NAME/KEY: MISC_FEATURE
<222> LOCATION: (4)..(4)
<223> OTHER INFORMATION: X est a basic amino acid
<220> FEATURE:
<221> NAME/KEY: MISC_FEATURE
<222> LOCATION: (5)..(5)
<223> OTHER INFORMATION: X is a hydroxy amino acid
<220> FEATURE:
<221> NAME/KEY: MISC_FEATURE
<222> LOCATION: (6)..(6)
<223> OTHER INFORMATION: X a hydroxy amino acid
<220> FEATURE:
<221> NAME/KEY: MISC_FEATURE
<222> LOCATION: (7)..(7)
<223> OTHER INFORMATION: X a basic amino acid
<220> FEATURE:
<221> NAME/KEY: MISC_FEATURE
<222> LOCATION: (8)..(8)
<223> OTHER INFORMATION: X a hydroxy amino acid
```

```
<400> SEQUENCE: 6

Xaa Xaa Xaa Xaa Xaa Xaa Xaa Xaa
1               5

<210> SEQ ID NO 7
<211> LENGTH: 4
<212> TYPE: PRT
<213> ORGANISM: Artificial Sequence
<220> FEATURE:
<223> OTHER INFORMATION: peptide d'adhision
<220> FEATURE:
<221> NAME/KEY: misc_feature
<223> OTHER INFORMATION: Synthetic
<220> FEATURE:
<221> NAME/KEY: MISC_FEATURE
<222> LOCATION: (1)..(1)
<223> OTHER INFORMATION: X a basic amino acid
<220> FEATURE:
<221> NAME/KEY: MISC_FEATURE
<222> LOCATION: (2)..(2)
<223> OTHER INFORMATION: X is a basic aminoacid
<220> FEATURE:
<221> NAME/KEY: MISC_FEATURE
<222> LOCATION: (3)..(3)
<223> OTHER INFORMATION: X is a hydroxy amino acid
<220> FEATURE:
<221> NAME/KEY: MISC_FEATURE
<222> LOCATION: (4)..(4)
<223> OTHER INFORMATION: X is a basic amino acid

<400> SEQUENCE: 7

Xaa Xaa Xaa Xaa
1

<210> SEQ ID NO 8
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 8

Tyr Ile Gly Ser Arg
1               5

<210> SEQ ID NO 9
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 9

Ile Lys Val Ala Val
1               5

<210> SEQ ID NO 10
<211> LENGTH: 6
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
```

```
<223> OTHER INFORMATION: Synthetic

<400> SEQUENCE: 10

Arg Tyr Trp Leu Pro Arg
1               5

<210> SEQ ID NO 11
<211> LENGTH: 10
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 11

Arg Asn Ile Ala Glu Ile Ile Lys Asp Ile
1               5                   10

<210> SEQ ID NO 12
<211> LENGTH: 4
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 12

Arg Glu Asp Val
1

<210> SEQ ID NO 13
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 13

Pro His Ser Arg Asn
1               5

<210> SEQ ID NO 14
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 14

Lys Asn Glu Glu Asp
1               5

<210> SEQ ID NO 15
<211> LENGTH: 5
<212> TYPE: PRT
<213> ORGANISM: Artificial Sequence
<220> FEATURE:
<223> OTHER INFORMATION: adhesion peptide
<220> FEATURE:
```

```
<221> NAME/KEY: misc_feature
<223> OTHER INFORMATION: Synthetic

<400> SEQUENCE: 15

Glu Ile Leu Asp Val
1               5

<210> SEQ ID NO 16
<211> LENGTH: 4
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 16

Lys Arg Ser Arg
1

<210> SEQ ID NO 17
<211> LENGTH: 7
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 17

Phe His Arg Arg Ile Lys Ala
1               5

<210> SEQ ID NO 18
<211> LENGTH: 4
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 18

Val Ala Pro Gly
1

<210> SEQ ID NO 19
<211> LENGTH: 6
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 19

Lys Gln Ala Gly Asp Val
1               5

<210> SEQ ID NO 20
<211> LENGTH: 4
<212> TYPE: PRT
<213> ORGANISM: Artificial Sequence
<220> FEATURE:
<223> OTHER INFORMATION: adhesion peptide
```

```
<220> FEATURE:
<221> NAME/KEY: misc_feature
<223> OTHER INFORMATION: Synthetic

<400> SEQUENCE: 20

Arg Gly Asp Ser
1

<210> SEQ ID NO 21
<211> LENGTH: 4
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 21

Gly Arg Gly Asp
1

<210> SEQ ID NO 22
<211> LENGTH: 4
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 22

Arg Gly Asp Val
1

<210> SEQ ID NO 23
<211> LENGTH: 4
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 23

Arg Gly Asp Thr
1

<210> SEQ ID NO 24
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 24

Gly Arg Gly Asp Gly
1               5

<210> SEQ ID NO 25
<211> LENGTH: 5
<212> TYPE: PRT
<213> ORGANISM: Artificial Sequence
<220> FEATURE:
```

```
<223> OTHER INFORMATION: adhesion peptide
<220> FEATURE:
<221> NAME/KEY: misc_feature
<223> OTHER INFORMATION: Synthetic

<400> SEQUENCE: 25

Gly Arg Gly Asp Tyr
1               5

<210> SEQ ID NO 26
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 26

Gly Arg Gly Asp Phe
1               5

<210> SEQ ID NO 27
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 27

Tyr Arg Gly Asp Ser
1               5

<210> SEQ ID NO 28
<211> LENGTH: 6
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 28

Tyr Arg Gly Asp Asp Gly
1               5

<210> SEQ ID NO 29
<211> LENGTH: 6
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 29

Gly Arg Gly Asp Ser Pro
1               5

<210> SEQ ID NO 30
<211> LENGTH: 6
<212> TYPE: PRT
<213> ORGANISM: Artificial Sequence
```

```
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 30

Gly Arg Gly Asp Ser Gly
1               5

<210> SEQ ID NO 31
<211> LENGTH: 6
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 31

Gly Arg Gly Asp Ser Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 32

Gly Arg Gly Asp Val Tyr
1               5

<210> SEQ ID NO 33
<211> LENGTH: 7
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 33

Gly Arg Gly Asp Ser Pro Lys
1               5

<210> SEQ ID NO 34
<211> LENGTH: 8
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 34

Cys Gly Arg Gly Asp Ser Pro Lys
1               5

<210> SEQ ID NO 35
<211> LENGTH: 8
<212> TYPE: PRT
```

```
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 35

Cys Gly Arg Gly Asp Ser Pro Lys
1               5

<210> SEQ ID NO 36
<211> LENGTH: 7
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 36

Cys Gly Arg Gly Asp Ser Tyr
1               5

<210> SEQ ID NO 37
<211> LENGTH: 5
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 37

Arg Gly Asp Phe Lys
1               5

<210> SEQ ID NO 38
<211> LENGTH: 8
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 38

Tyr Ala Val Thr Gly Arg Gly Asp
1               5

<210> SEQ ID NO 39
<211> LENGTH: 16
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 39

Ala Cys Cys Gly Gly Asn Gly Glu Pro Arg Gly Asp Tyr Arg Ala Tyr
1               5                   10                  15

<210> SEQ ID NO 40
<211> LENGTH: 13
```

```
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 40

Ala Cys Gly Cys Gly Tyr Gly Arg Gly Asp Ser Pro Gly
1               5                   10

<210> SEQ ID NO 41
<211> LENGTH: 9
<212> TYPE: PRT
<213> ORGANISM: Artificial Sequence
<220> FEATURE:
<223> OTHER INFORMATION: adhesion peptide
<220> FEATURE:
<221> NAME/KEY: misc_feature
<223> OTHER INFORMATION: Synthetic

<400> SEQUENCE: 41

Arg Gly Asp Pro Ala Ser Ser Lys Pro
1               5

<210> SEQ ID NO 42
<211> LENGTH: 16
<212> TYPE: PRT
<213> ORGANISM: Artificial Sequence
<220> FEATURE:
<223> OTHER INFORMATION: Synthetic

<400> SEQUENCE: 42

Cys Gly Ser Gly Gly Gly Gly Gly Gly Ser Gly Arg Gly Asp Ser
1               5                   10                  15
```